(12) United States Patent
Cho et al.

(10) Patent No.: US 10,032,996 B2
(45) Date of Patent: Jul. 24, 2018

(54) HETERO-CYCLIC COMPOUND AND ORGANIC LIGHT EMITTING DEVICE INCLUDING THE SAME

(71) Applicant: LG CHEM, LTD., Seoul (KR)

(72) Inventors: Seongmi Cho, Daejeon (KR); Hoyong Lee, Daejeon (KR); Sang Young Jeon, Daejeon (KR); Hyoung Seok Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 407 days.

(21) Appl. No.: 14/843,636

(22) Filed: Sep. 2, 2015

(65) Prior Publication Data
US 2016/0072079 A1    Mar. 10, 2016

(30) Foreign Application Priority Data
Sep. 5, 2014    (KR) .......................... 10-2014-0119126

(51) Int. Cl.
| | | |
|---|---|---|
| *H01L 51/50* | (2006.01) | |
| *H01L 51/00* | (2006.01) | |
| *C07D 209/86* | (2006.01) | |
| *C09K 11/02* | (2006.01) | |
| *C07D 409/10* | (2006.01) | |

(52) U.S. Cl.
CPC ........ *H01L 51/0072* (2013.01); *C07D 209/86* (2013.01); *C07D 409/10* (2013.01); *C09K 11/025* (2013.01); *H01L 51/0054* (2013.01); *H01L 51/0058* (2013.01); *H01L 51/0074* (2013.01); *H01L 51/0085* (2013.01); *H01L 51/5016* (2013.01); *H01L 2251/308* (2013.01)

(58) Field of Classification Search
None
See application file for complete search history.

(56) References Cited

U.S. PATENT DOCUMENTS

2017/0077423 A1*  3/2017  Ahn ................... H01L 51/0072

FOREIGN PATENT DOCUMENTS

| JP | 2011241160 A | 12/2011 | |
|---|---|---|---|
| KR | 20000051826 A | 8/2000 | |
| WO | 2013-109045 A1 | 7/2013 | |
| WO | WO 2014061991 | * 4/2014 | ............. H01L 51/54 |

* cited by examiner

*Primary Examiner* — Gregory D Clark
(74) *Attorney, Agent, or Firm* — Dentons US LLP

(57) ABSTRACT

The present specification provides a hetero-cyclic compound and an organic light emitting device including the same.

12 Claims, 5 Drawing Sheets

[Figure 1]
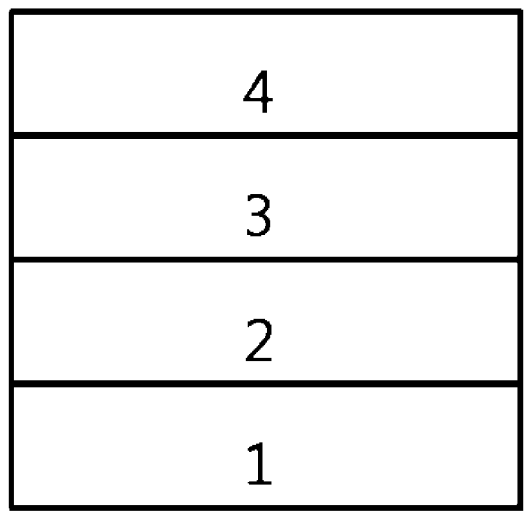
[Figure 2]
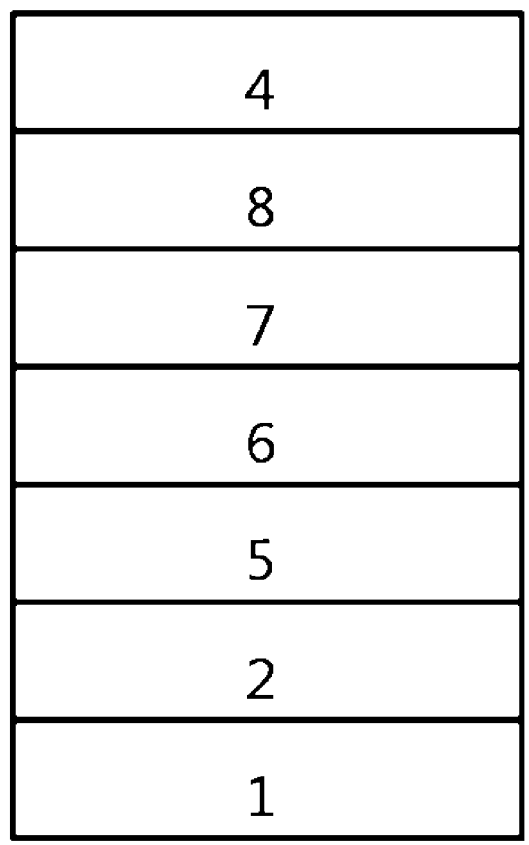

[Figure 3]
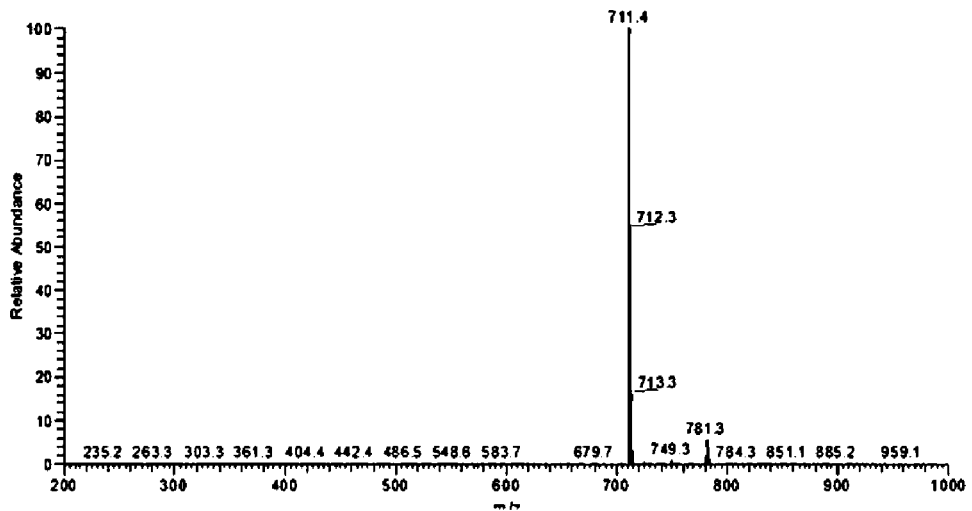
[Figure 4]
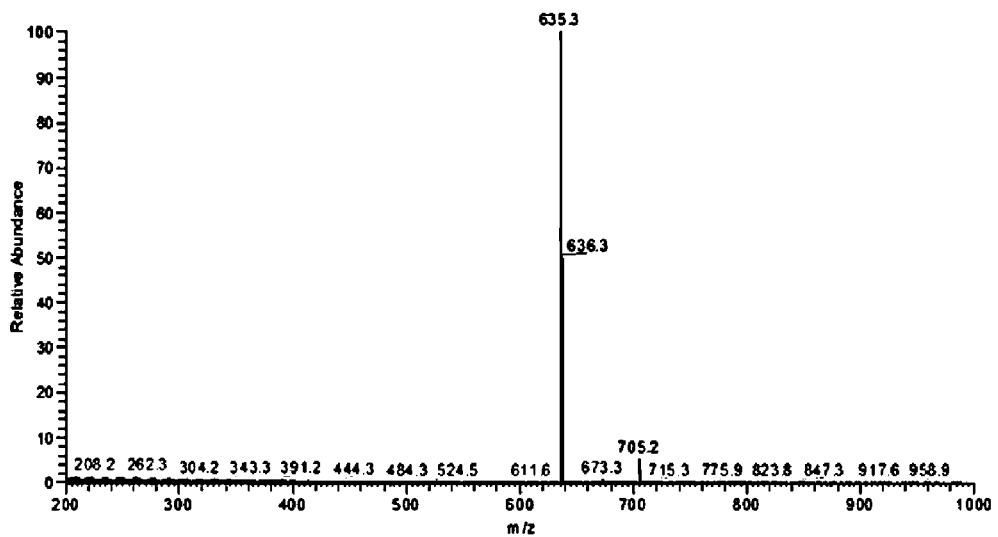

[Figure 5]
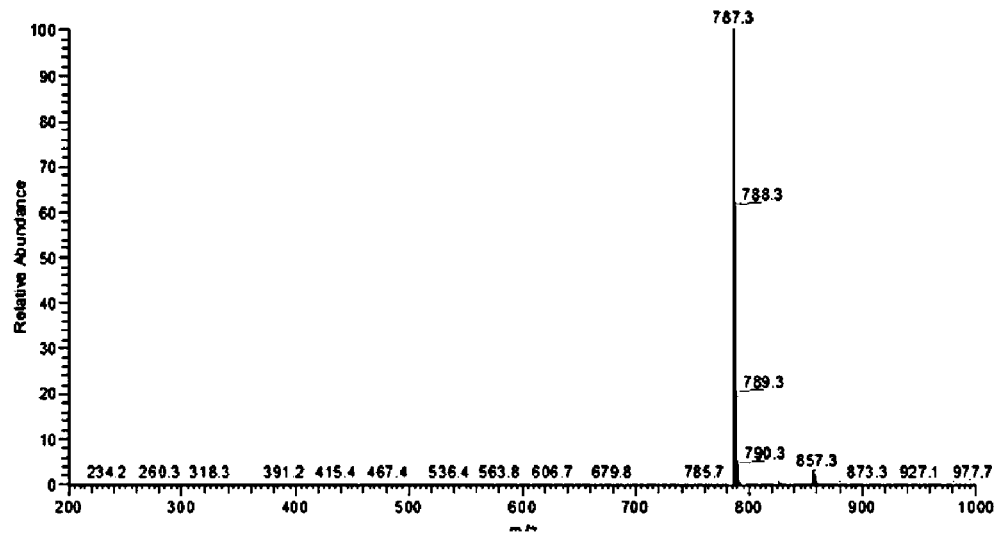
[Figure 6]
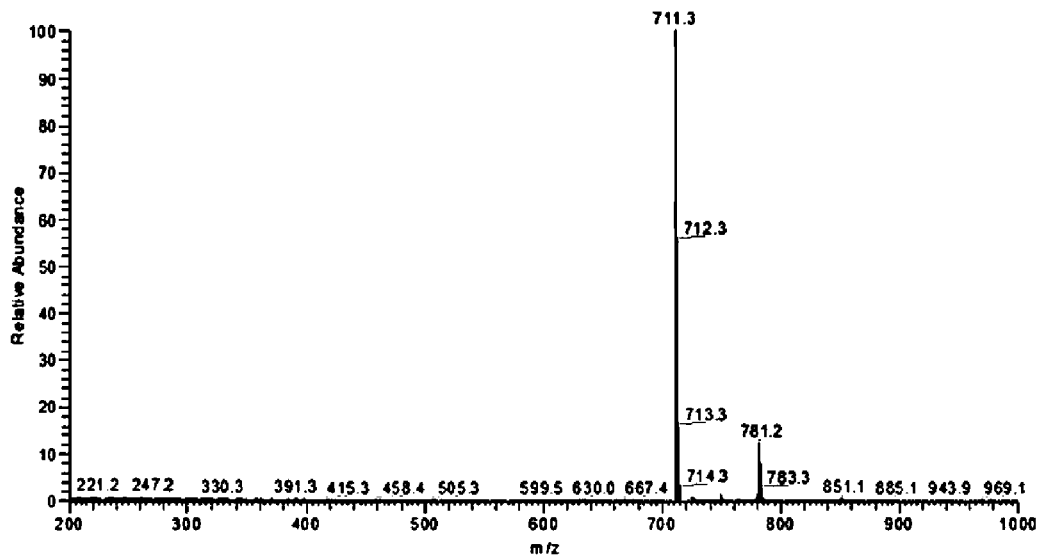

[Figure 7]
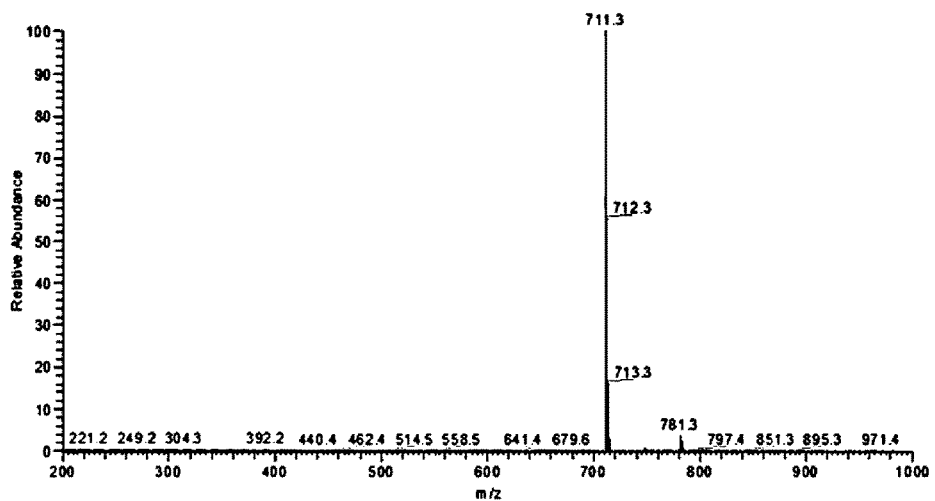
[Figure 8]
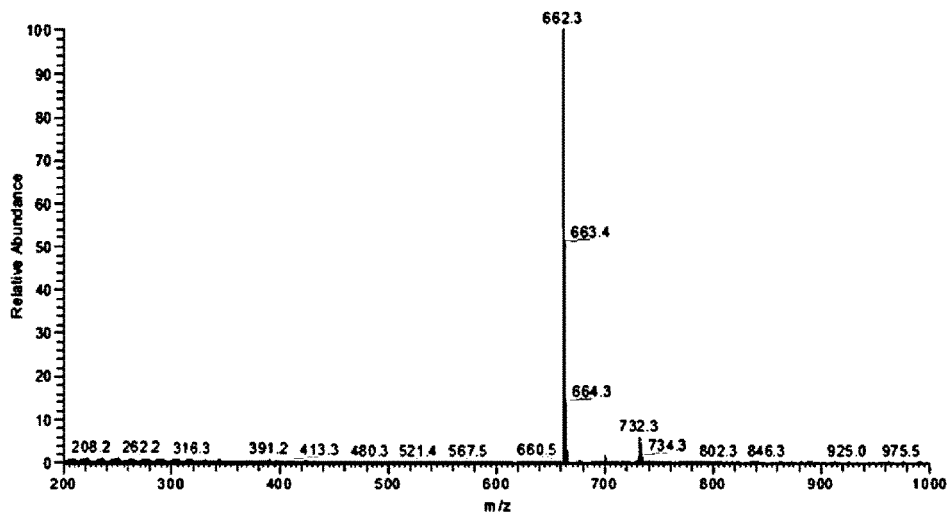

[Figure 9]
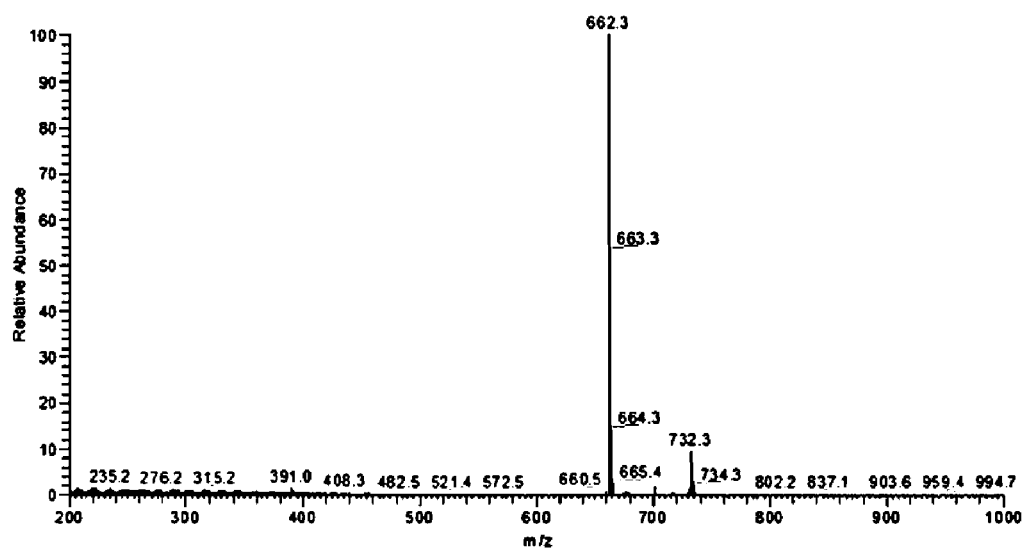

HETERO-CYCLIC COMPOUND AND ORGANIC LIGHT EMITTING DEVICE INCLUDING THE SAME

This application claims the benefit of Korean Application No. 10-2014-0119126, filed Sep. 5, 2014, which is hereby incorporated by reference in its entirety for all purposes as if fully set forth herein.

FIELD OF THE INVENTION

The present specification relates to a hetero-cyclic compound and an organic light emitting device including the same.

BACKGROUND OF THE INVENTION

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents (Patent Document 1) Korean Patent Application Laid-Open Publication No. 2000-0051826

SUMMARY OF THE INVENTION

The present specification describes a hetero-cyclic compound and an organic light emitting device including the same.

One embodiment of the present specification provides a compound represented by the following Chemical Formula 1:

[Chemical Formula 1]

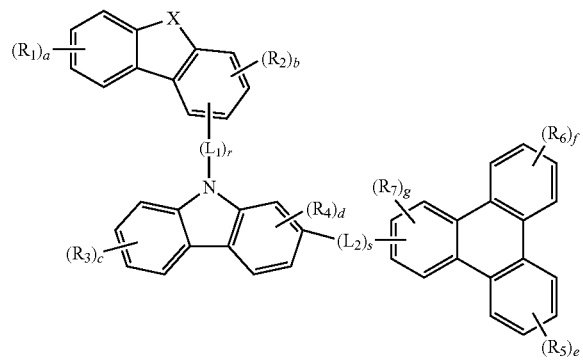

In Chemical Formula 1,

X is O, S, NAr, $CR_{11}R_{12}$ or $SiR_{13}R_{14}$, $L_1$ and $L_2$ are the same as or different from each other, and each independently a direct bond, substituted or unsubstituted arylene, or substituted or unsubstituted heteroarylene including one or more of O and S atoms, $R_1$ to $R_7$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted hetero-cyclic group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, Ar is a substituted or unsubstituted aryl group or heteroaryl group, $R_{11}$ to $R_{14}$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; or a substituted or unsubstituted hetero-cyclic group, or $R_{11}$ and $R_{12}$ or $R_{13}$ and $R_{14}$ bond to each other to form a substituted or unsubstituted hydrocarbon ring or heteroring, a, c, e and f are the same as or different from each other, and each independently an integer of 0 to 4, b, d and g are the same as or different from each other, and each independently an integer of 0 to 3, r and s are the same as or different from each other, and each independently an integer of 0 to 5, when a is two or greater, $R_1$s are the same as or different from each other, when b is two or greater, $R_2$s are the same as or different from each other, when c is two or greater, $R_3$s are the same as or different from each other, when d is two or greater, $R_4$s are the same as or different from each other, when e is two or greater, $R_5$s are the same as or different from each other, when f is two or greater, $R_6$s are the same as or different from each other, when g is two or greater, $R_7$s are the same as or different from each other, when r is two or greater, $L_1$s are the same as or different from each other, and when s is two or greater, $L_2$s are the same as or different from each other.

In addition, one embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

BRIEF DESCRIPTION OF THE DRAWINGS

The objects and qualities of the present invention will become apparent from the following description of embodiments given in conjunction with the accompanying drawings, in which:

FIG. 1 is a diagram showing an example of an organic light emitting device formed with a substrate (1), an anode (2), a light emitting layer (3) and a cathode (4);

FIG. 2 is a diagram showing an example of an organic light emitting device formed with a substrate (1), an anode (2), a hole injection layer (5), a hole transfer layer (6), a light emitting layer (7), an electron transfer layer (8) and a cathode (4);

FIG. 3 shows an MS result, a material identifying the synthesis of Chemical Formula 1-1;

FIG. 4 shows an MS result, a material identifying the synthesis of Chemical Formula 1-2;

FIG. 5 shows an MS result, a material identifying the synthesis of Chemical Formula 1-3;

FIG. 6 shows an MS result, a material identifying the synthesis of Chemical Formula 1-4;

FIG. 7 shows an MS result, a material identifying the synthesis of Chemical Formula 1-10;

FIG. 8 shows an MS result, a material identifying the synthesis of Chemical Formula 1-13; and FIG. 9 shows an MS result, a material identifying the synthesis of Chemical Formula 1-14.

1: Substrate
2: Anode
3: Light Emitting Layer
4: Cathode
5: Hole Injection Layer
6: Hole Transfer Layer
7: Light Emitting Layer
8: Electron Transfer Layer

DETAILED DESCRIPTION OF THE EMBODIMENTS

Hereinafter, the present specification will be described in more detail.

One embodiment of the present specification provides a compound represented by Chemical Formula 1.

In the present specification,  means a bond linking to other substituents.

Examples of the substituents are described below, however, the substituents are not limited thereto.

The term "substituted or unsubstituted" in the present specification means being substituted with one or more substituents selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a hetero-cyclic group including one or more of N, O and S atoms, or having no substituents, or being substituted with a substituent linking two or more substituents of the substituents illustrated above, or having no substituents. For example, "a substituent linking two or more substituents" may include a biphenyl group. In other words, a biphenyl group may be interpreted as an aryl group, or as a substituent linking two phenyl groups.

In the present specification, an "adjacent" group may mean a substituent substituting an atom directly linking to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as "adjacent" groups.

In the present specification, the number of carbon atoms of the carbonyl group is not particularly limited, but is preferably 1 to 40. Specifically, compounds having structures such as below may be included, but the compound is not limited thereto.

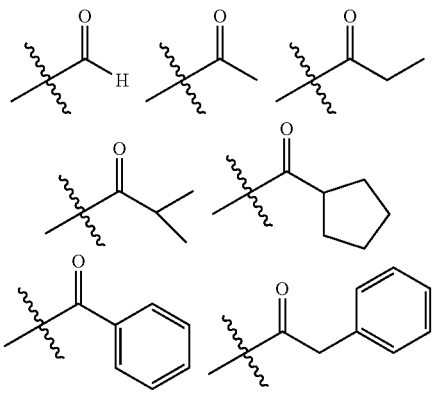

In the present specification, in the ester group, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the compound is not limited thereto.

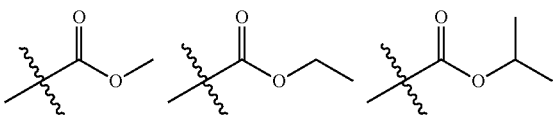

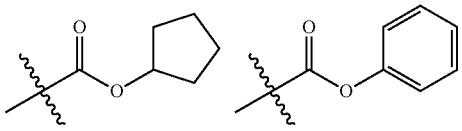

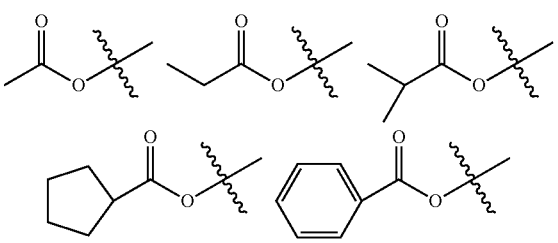

In the present specification, the number of carbon atoms of the imide group is not particularly limited, but is preferably 1 to 25. Specifically, compounds having structures such as below may be included, but the compound is not limited thereto.

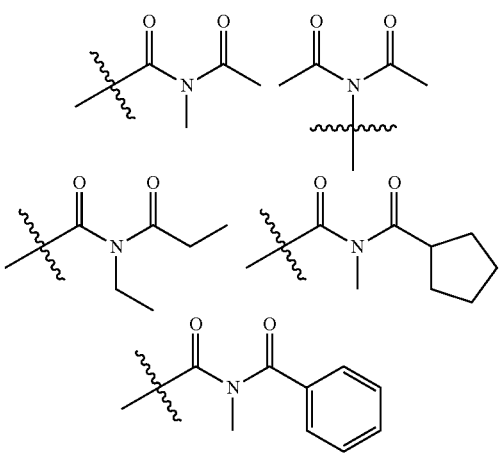

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, the boron group specifically includes a trimethylboron group, a triethylboron group, a t-butyldimethylboron group, a triphenylboron group, a phenylboron group and the like, but is not limited thereto.

In the present specification, examples of the halogen group include fluorine, chlorine, bromine or iodine.

In the present specification, the alkyl group may be linear or branched, and the number of carbon atoms is not particularly limited, but is preferably 1 to 40. According to one embodiment, the alkyl group has 1 to 20 carbon atoms. According to another embodiment, the alkyl group has 1 to 10 carbon atoms. According to another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the alkenyl group may be linear or branched, and although not particularly limited, the number of carbon atoms is preferably 2 to 40. According to one embodiment, the alkenyl group has 2 to 20 carbon atoms. According to another embodiment, the alkenyl group has 2 to 10 carbon atoms. According to another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the aryl group is not particularly limited, but preferably has 6 to 60 carbon atoms, and may be a monocyclic aryl group or a multicyclic aryl group. According to one embodiment, the aryl group has 6 to 30 carbon atoms. According to one embodiment, the aryl group has 6 to 20 carbon atoms. Examples of the aryl group as a monocyclic aryl group may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a crycenyl group, a fluorenyl group and the like, but are not limited thereto.

In the present specification, the fluorenyl group may be substituted, and two substituents may bond to each other to form a spiro structure.

When the fluorenyl group is substituted,

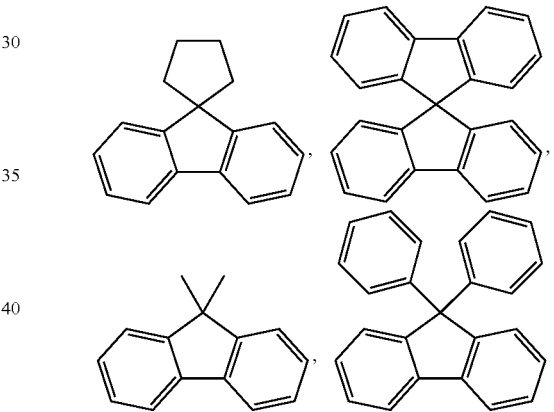

and the like may be included. However, the structure is not limited thereto.

In the present specification, the hetero-cyclic group is a hetero-cyclic group including one or more of O, N and S as a heteroatom, and although not particularly limited, the number of carbon atoms is preferably 2 to 60. Examples of the hetero-cyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, the aryl group in the aralkyl group, the aralkenyl group, the alkylaryl group and the arylamine group is the same as the examples of the aryl group described above.

In the present specification, the alkyl group in the aralkyl group, the alkylaryl group and the alkylamine group is the same as the examples of the alkyl group described above.

In the present specification, the descriptions on the heterocyclic group made above may be used for the heteroaryl in the heteroarylamine.

In the present specification, the alkenyl group in the aralkenyl group is the same as the examples of the alkenyl group described above.

In the present specification, the descriptions on the aryl group made above may be used for the arylene except that the arylene is a divalent group.

In the present specification, the descriptions on the heterocyclic group made above may be used for the heteroarylene except that the heteroarylene is a divalent group.

According to one embodiment of the present specification, Ar is a substituted or unsubstituted aryl group.

According to one embodiment of the present specification, Ar is a one-membered to five-membered substituted or unsubstituted aryl group.

According to one embodiment of the present specification, Ar is a one-membered to three-membered substituted or unsubstituted aryl group.

According to one embodiment of the present specification, Ar is a substituted or unsubstituted phenyl group; a substituted or unsubstituted biphenyl group; or a substituted or unsubstituted naphthyl group.

According to one embodiment of the present specification, Chemical Formula 1 may be represented by any one of the following Chemical Formulae 2 to 4.

[Chemical Formula 2]

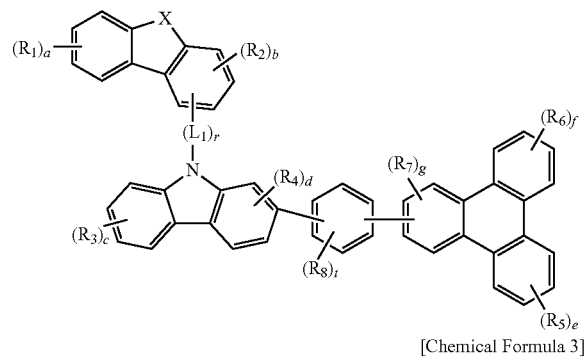

[Chemical Formula 3]

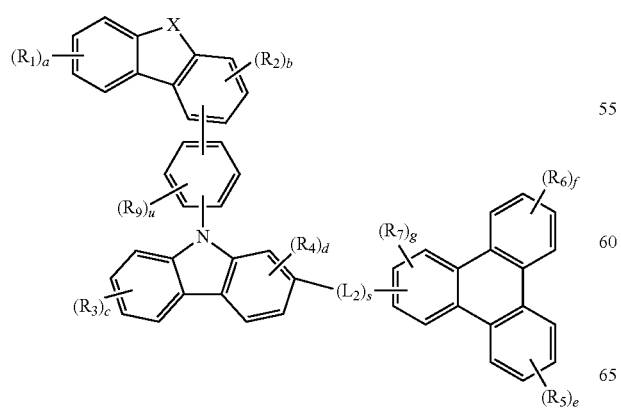

[Chemical Formula 4]

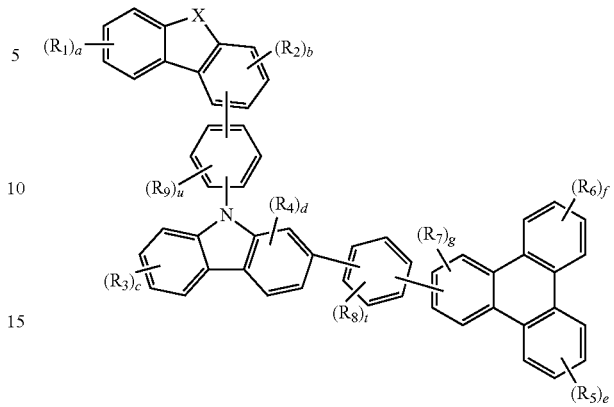

In Chemical Formulae 2 to 4, definitions of X, $R_1$ to $R_7$, $L_1$, $L_2$, a, b, c, d, e, f, g, r and s are the same as in Chemical Formula 1, $R_8$ and $R_9$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted hetero-cyclic group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, t and u are the same as or different from each other, and are each an integer of 0 to 4, when t is two or greater, $R_8$s are the same as or different from each other, and when u is two or greater, $R_9$s are the same as or different from each other.

According to one embodiment of the present specification, Chemical Formula 1 may be represented by the following Chemical Formula 5 or 6.

[Chemical Formula 5]

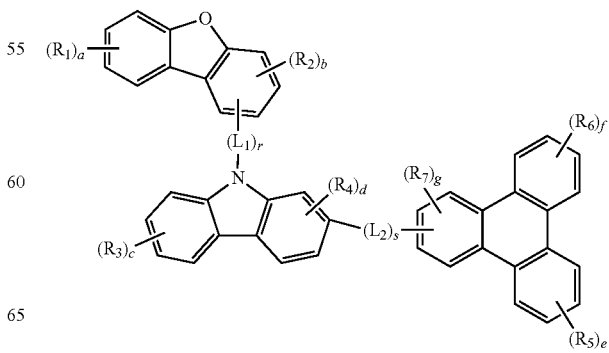

-continued

[Chemical Formula 6]

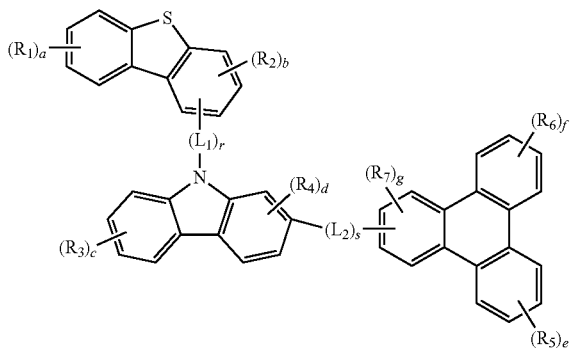

In Chemical Formulae 5 and 6,
definitions of $R_1$ to $R_7$, $L_1$, $L_2$, a, b, c, d, e, f, g, r and s are the same as in Chemical Formula 1.

According to one embodiment of the present specification, Chemical Formula 1 may be represented by the following Chemical Formula 7.

[Chemical Formula 7]

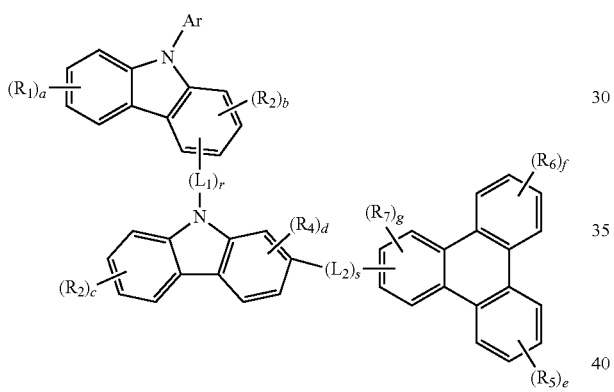

In Chemical Formula 7,
definitions of $R_1$ to $R_7$, $L_1$, $L_2$, Ar, a, b, c, d, e, f, g, r and s are the same as in Chemical Formula 1.

According to one embodiment of the present specification, Chemical Formula 1 may be represented by the following Chemical Formula 8.

[Chemical Formula 8]

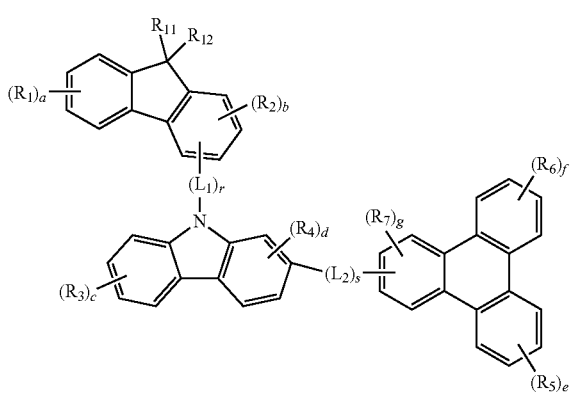

In Chemical Formula 8,
definitions of $R_1$ to $R_7$, $L_1$, $L_2$, $R_{11}$, $R_{12}$, a, b, c, d, e, f, g, r and s are the same as in Chemical Formula 1.

According to one embodiment of the present specification, Chemical Formula 1 may be represented by the following Chemical Formula 9.

[Chemical Formula 9]

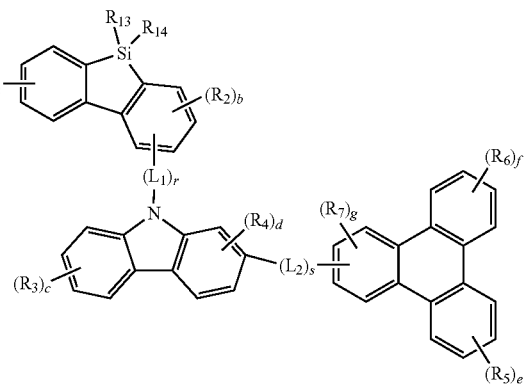

In Chemical Formula 9,
definitions of $R_1$ to $R_7$, $L_1$, $L_2$, $R_{13}$, $R_{14}$, a, b, c, d, e, f, g, r and s are the same as in Chemical Formula 1.

In the present specification, a triphenylene group is represented by the following drawing.

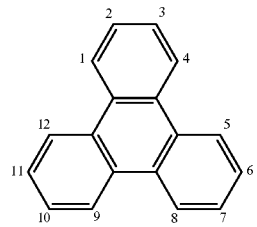

According to one embodiment of the present specification, $L_2$ bonds to position 2 of the triphenylene group in Chemical Formula 1. When the remaining structure of Chemical Formula 1 bonds to position 2 of the triphenylene group, synthesis is readily carried out and electron mobility is favorable compared to other positions due to lengthened conjugation. When the triphenylene group is not present, electron mobility and affinity decrease in the compound, and holes and electrons are not balanced in a light emitting layer.

According to one embodiment of the present specification, $L_1$ and $L_2$ are the same as or different from each other, and each independently a direct bond, substituted or unsubstituted arylene, or substituted or unsubstituted heteroarylene including one or more of O and S atoms.

According to one embodiment of the present specification, $L_1$ and $L_2$ are the same as or different from each other, and are a direct bond, or substituted or unsubstituted arylene.

According to one embodiment of the present specification, $L_1$ and $L_2$ are the same as or different from each other, and are a direct bond, substituted or unsubstituted phenylene, substituted or unsubstituted naphthylene, substituted or unsubstituted biphenylene, or substituted or unsubstituted fluorenylene.

According to one embodiment of the present specification, $L_1$ and $L_2$ are the same as or different from each other, and are a direct bond, phenylene, naphthylene, biphenylene, or fluorenylene unsubstituted or substituted with an alkyl group.

According to one embodiment of the present specification, $L_1$ and $L_2$ are the same as or different from each other, and are a direct bond, phenylene, naphthylene, biphenylene, or fluorenylene substituted with a methyl group.

According to one embodiment of the present specification, $L_1$ and $L_2$ are a direct bond or phenylene.

According to one embodiment of the present specification, $L_1$ and $L_2$ are a direct bond.

According to one embodiment of the present specification, $L_1$ is phenylene, and $L_2$ is a direct bond.

According to one embodiment of the present specification, $L_1$ is a direct bond, and $L_2$ is phenylene.

According to one embodiment of the present specification, $L_1$ is phenylene, and $L_2$ is phenylene.

According to one embodiment of the present specification, $R_1$ is hydrogen; deuterium; a substituted or unsubstituted alkyl group; a substituted or unsubstituted cycloalkyl group; or a substituted or unsubstituted aryl group.

According to one embodiment of the present specification, $R_1$ is hydrogen; deuterium; a substituted or unsubstituted alkyl group; or a substituted or unsubstituted cycloalkyl group.

According to one embodiment of the present specification, $R_1$ is hydrogen; or deuterium.

According to one embodiment of the present specification, $R_2$ is hydrogen; deuterium; a substituted or unsubstituted alkyl group; a substituted or unsubstituted cycloalkyl group; or a substituted or unsubstituted aryl group.

According to one embodiment of the present specification, $R_2$ is hydrogen; deuterium; a substituted or unsubstituted alkyl group; or a substituted or unsubstituted cycloalkyl group.

According to one embodiment of the present specification, $R_2$ is hydrogen; or deuterium.

According to one embodiment of the present specification, $R_3$ is hydrogen; deuterium; a substituted or unsubstituted alkyl group; a substituted or unsubstituted cycloalkyl group; or a substituted or unsubstituted aryl group.

According to one embodiment of the present specification, $R_3$ is hydrogen; deuterium; a substituted or unsubstituted alkyl group; or a substituted or unsubstituted cycloalkyl group.

According to one embodiment of the present specification, $R_3$ is hydrogen; or deuterium.

According to one embodiment of the present specification, $R_4$ is hydrogen; deuterium; a substituted or unsubstituted alkyl group; a substituted or unsubstituted cycloalkyl group; or a substituted or unsubstituted aryl group.

According to one embodiment of the present specification, $R_4$ is hydrogen; deuterium; a substituted or unsubstituted alkyl group; or a substituted or unsubstituted cycloalkyl group.

According to one embodiment of the present specification, $R_4$ is hydrogen; or deuterium.

According to one embodiment of the present specification, $R_5$ is hydrogen; deuterium; a substituted or unsubstituted alkyl group; a substituted or unsubstituted cycloalkyl group; or a substituted or unsubstituted aryl group.

According to one embodiment of the present specification, $R_5$ is hydrogen; deuterium; a substituted or unsubstituted alkyl group; or a substituted or unsubstituted cycloalkyl group.

According to one embodiment of the present specification, $R_5$ is hydrogen; or deuterium.

According to one embodiment of the present specification, $R_6$ is hydrogen; deuterium; a substituted or unsubstituted alkyl group; a substituted or unsubstituted cycloalkyl group; or a substituted or unsubstituted aryl group.

According to one embodiment of the present specification, $R_6$ is hydrogen; deuterium; a substituted or unsubstituted alkyl group; or a substituted or unsubstituted cycloalkyl group.

According to one embodiment of the present specification, $R_6$ is hydrogen; or deuterium.

According to one embodiment of the present specification, $R_7$ is hydrogen; deuterium; a substituted or unsubstituted alkyl group; a substituted or unsubstituted cycloalkyl group; or a substituted or unsubstituted aryl group.

According to one embodiment of the present specification, $R_7$ is hydrogen; deuterium; a substituted or unsubstituted alkyl group; or a substituted or unsubstituted cycloalkyl group.

According to one embodiment of the present specification, $R_7$ is hydrogen; or deuterium.

According to one embodiment of the present specification, $R_{11}$ and $R_{12}$ are the same as or different from each other, and each independently a substituted or unsubstituted alkyl group; or a substituted or unsubstituted aryl group, or bond to each other to form a ring.

According to one embodiment of the present specification, $R_{11}$ and $R_{12}$ are the same as or different from each other, and each independently a substituted or unsubstituted alkyl group having 1 to 6 carbon atoms; or a substituted or unsubstituted phenyl group, or bond to each other to form a substituted or unsubstituted fluorenyl group.

According to one embodiment of the present specification, $R_{11}$ and $R_{12}$ are the same as or different from each other, and each independently an alkyl group having 1 to 6 carbon atoms; or a phenyl group, or bond to each other to form a fluorenyl group, a dimethylfluorenyl group, a diphenylfluorenyl group or a spirobifluorenyl group.

According to one embodiment of the present specification, $R_{11}$ and $R_{12}$ are each an alkyl group having 1 to 6 carbon atoms.

According to one embodiment of the present specification, $R_{11}$ and $R_{12}$ are each a methyl group.

According to one embodiment of the present specification, $R_{13}$ and $R_{14}$ are the same as or different from each other, and each independently a substituted or unsubstituted alkyl group; or a substituted or unsubstituted aryl group, or bond to each other to form a ring.

According to one embodiment of the present specification, $R_{13}$ and $R_{14}$ are the same as or different from each other, and each independently a substituted or unsubstituted alkyl group having 1 to 6 carbon atoms; or a substituted or unsubstituted phenyl group, or bond to each other to form a substituted or unsubstituted fluorenyl group.

According to one embodiment of the present specification, $R_{13}$ and $R_{14}$ are the same as or different from each other, and each independently an alkyl group having 1 to 6 carbon atoms; or a phenyl group, or bond to each other to form a fluorenyl group, a dimethylfluorenyl group, a diphenylfluorenyl group or a spirobifluorenyl group.

According to one embodiment of the present specification, $R_{13}$ and $R_{14}$ are each an alkyl group having 1 to 6 carbon atoms.

According to one embodiment of the present specification, $R_{13}$ and $R_{14}$ are each a methyl group.

According to one embodiment of the present invention, the compound of Chemical Formula 1 may be selected from the following structures.

Chemical Formula 1-1

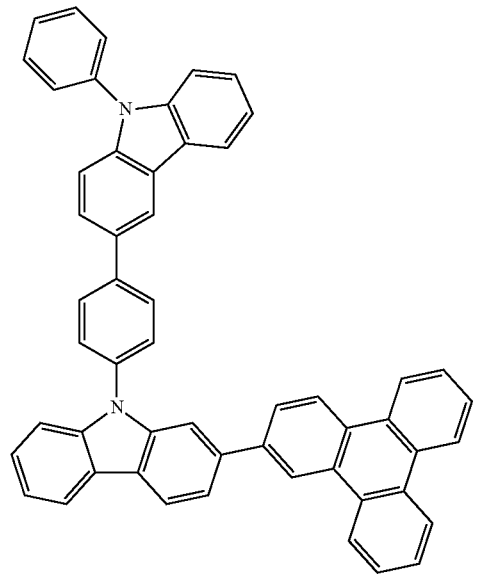

Chemical Formula 1-2

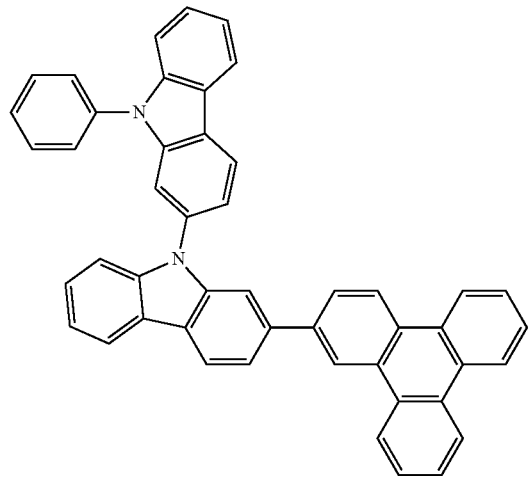 [SMILES: c1ccc(-n2c3ccccc3c3ccc(-n4c5ccccc5c5ccc(-c6ccc7c8ccccc8c8ccccc8c7c6)cc54)cc32)cc1]

Chemical Formula 1-3

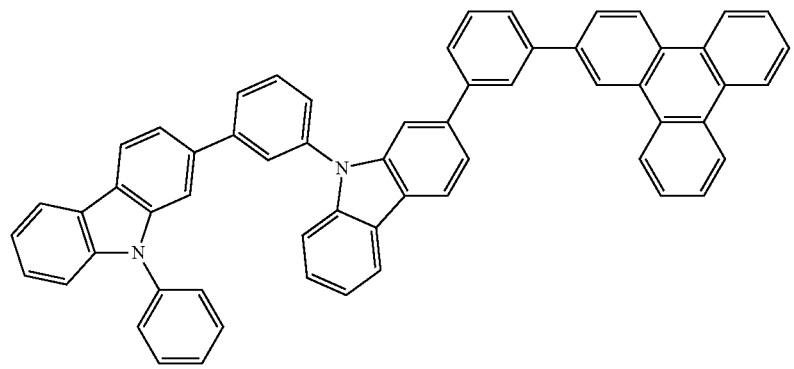

Chemical Formula 1-4

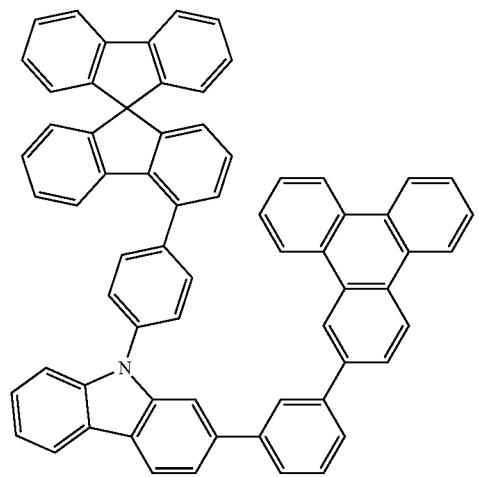

Chemical Formula 1-5

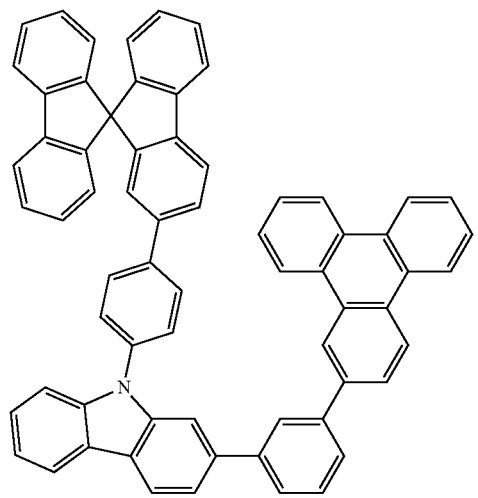

-continued
Chemical Formula 1-6
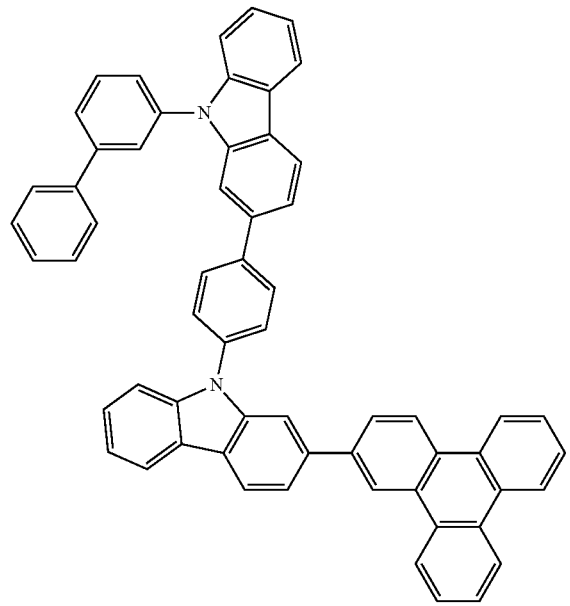
Chemical Formula 1-7
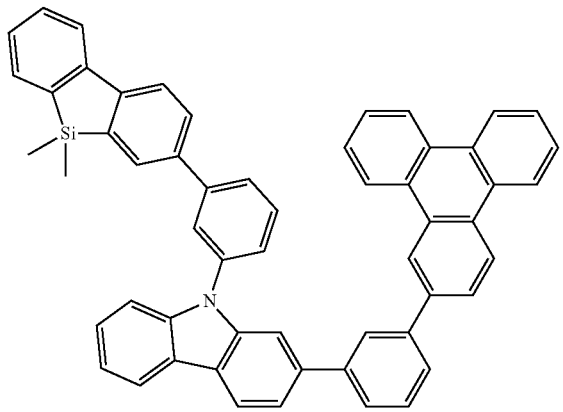
Chemical Formula 1-8
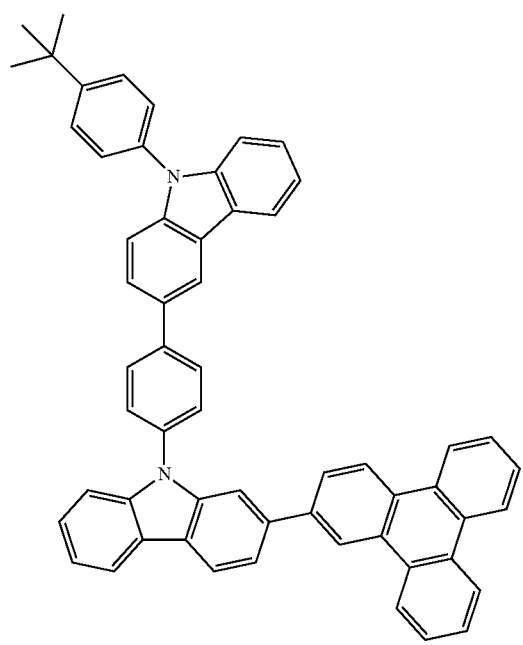
Chemical Formula 1-9
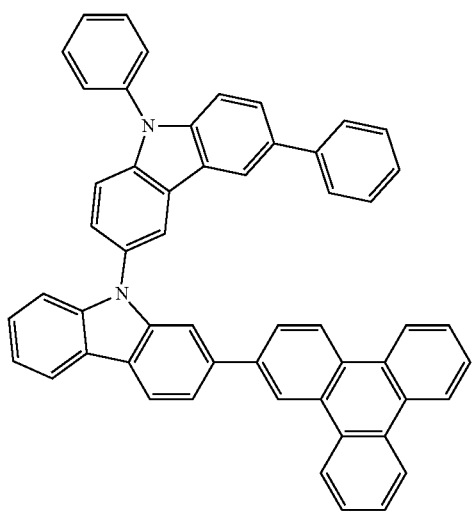

-continued
Chemical Formula 1-10
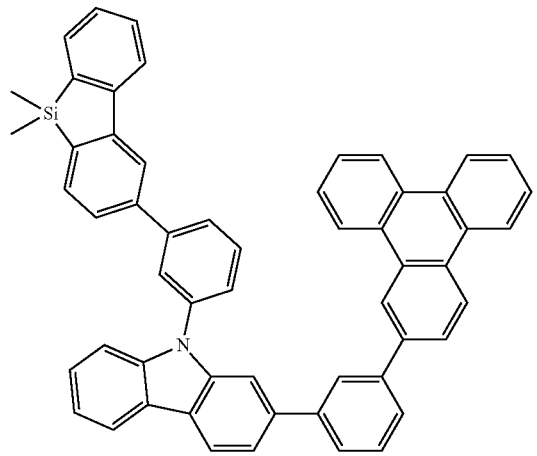
Chemical Formula 1-11
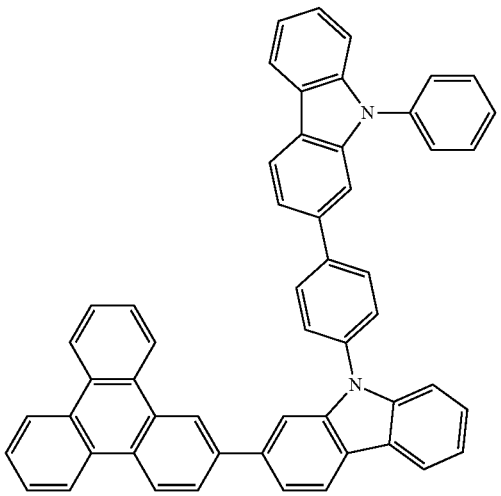
Chemical Formula 1-12
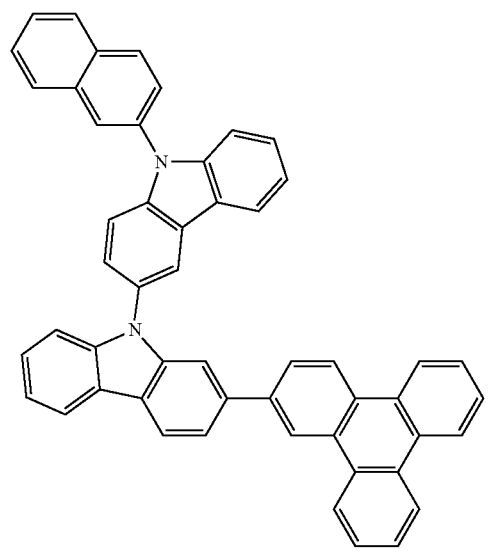
Chemical Formula 1-13
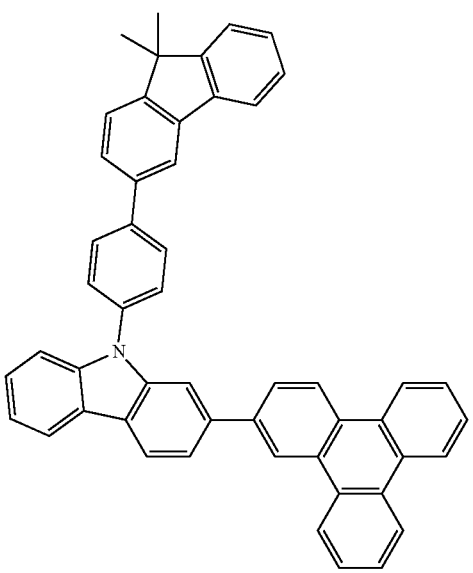
Chemical Formula 1-14
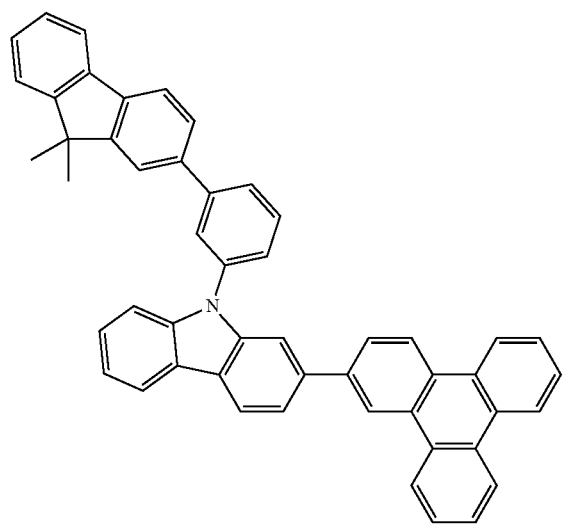
Chemical Formula 1-15
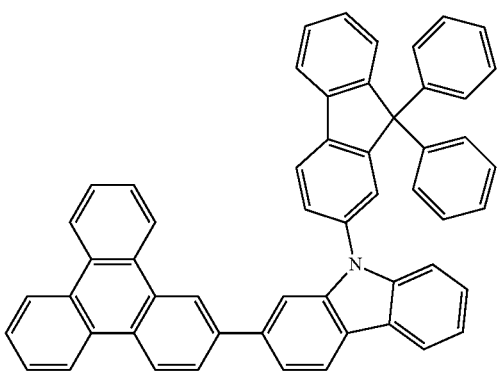

-continued
Chemical Formula 1-16
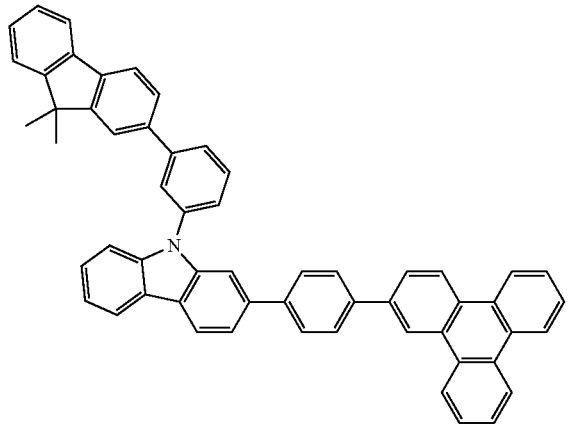
Chemical Formula 1-17
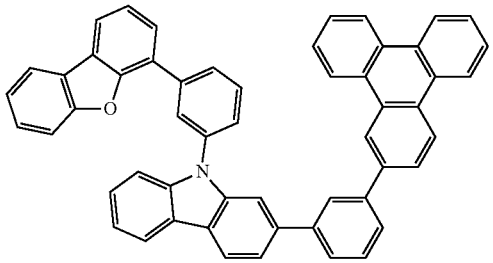
Chemical Formula 1-18
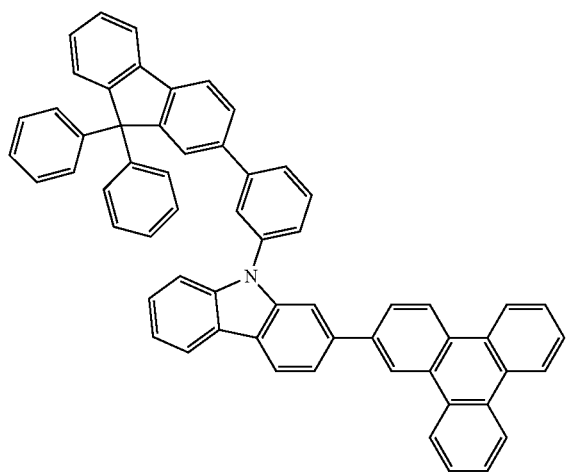
Chemical Formula 1-19
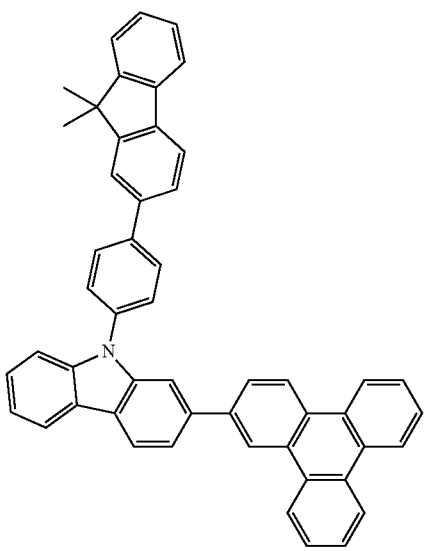
Chemical Formula 1-20
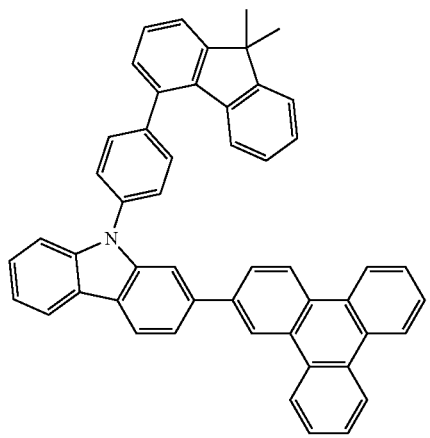
Chemical Formula 1-21
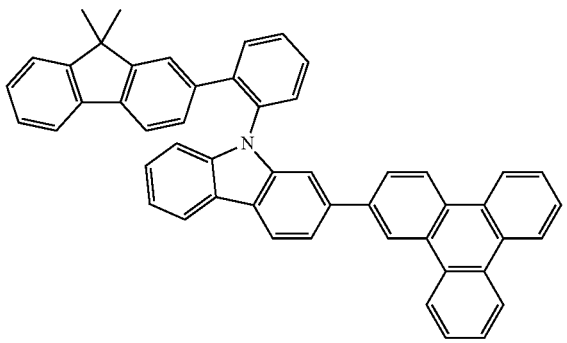

Chemical Formula 1-22
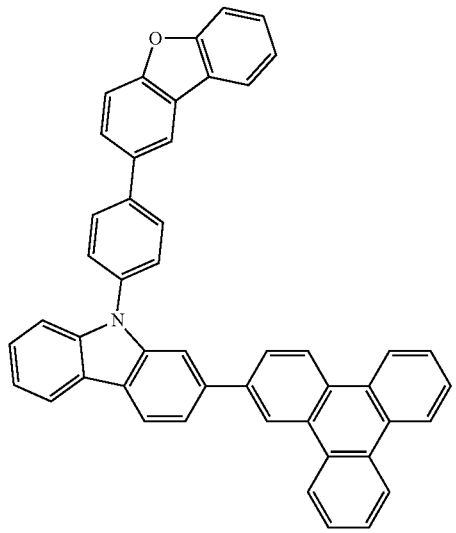
Chemical Formula 1-23
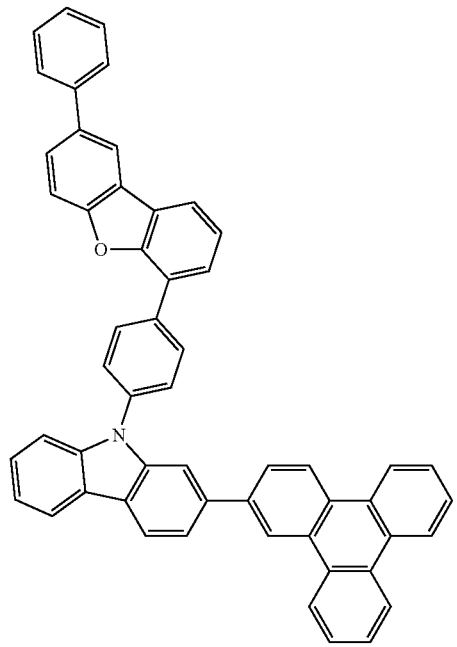
Chemical Formula 1-24
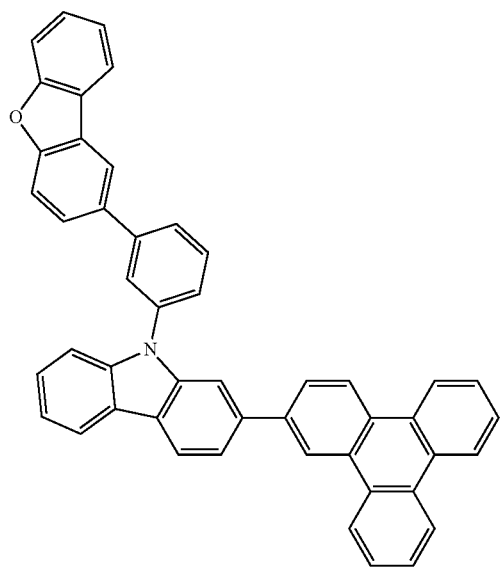
Chemical Formula 1-25
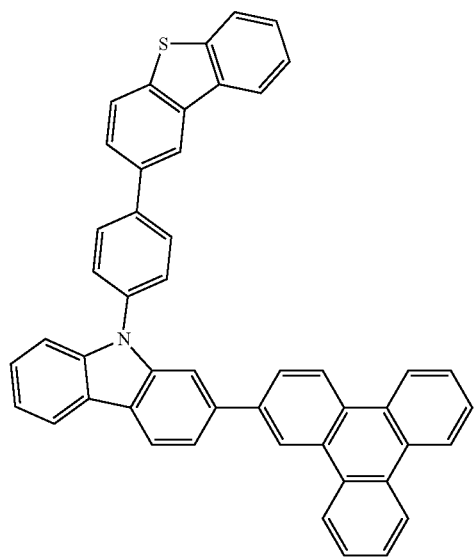

-continued
Chemical Formula 1-26
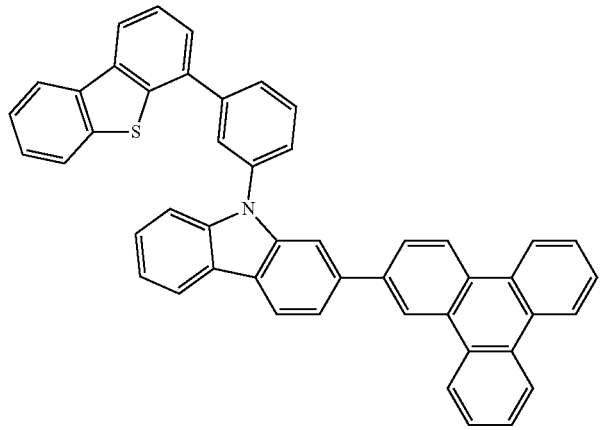
Chemical Formula 1-27
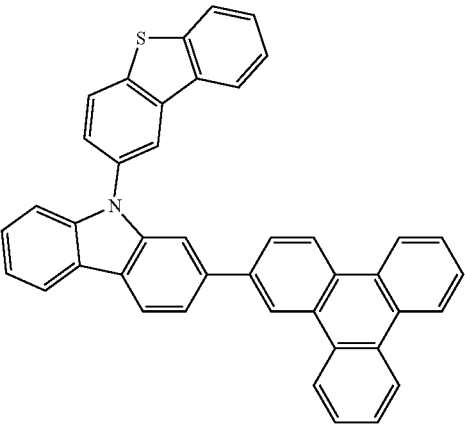
Chemical Formula 1-28
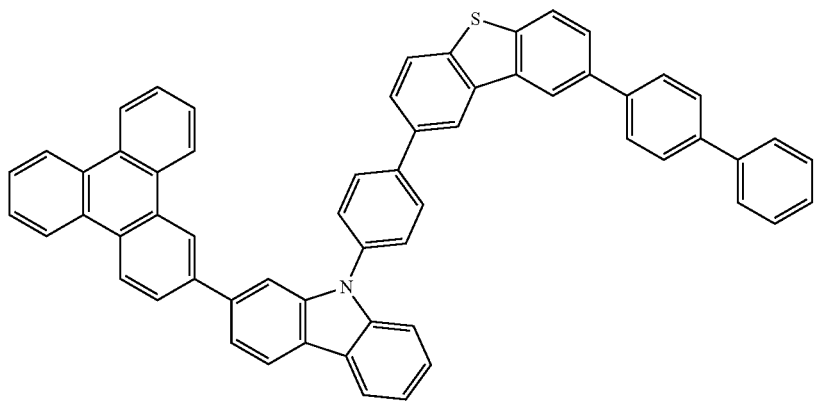
Chemical Formula 1-29
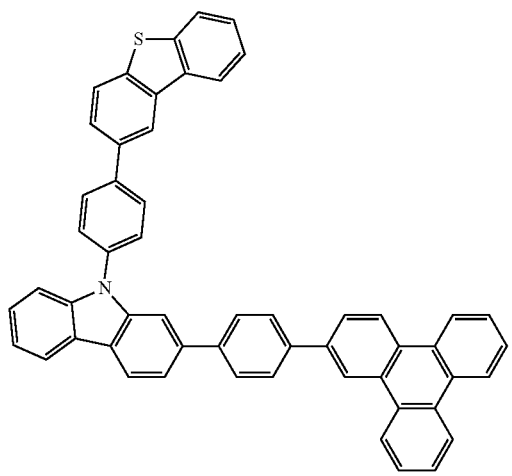
Chemical Formula 1-30
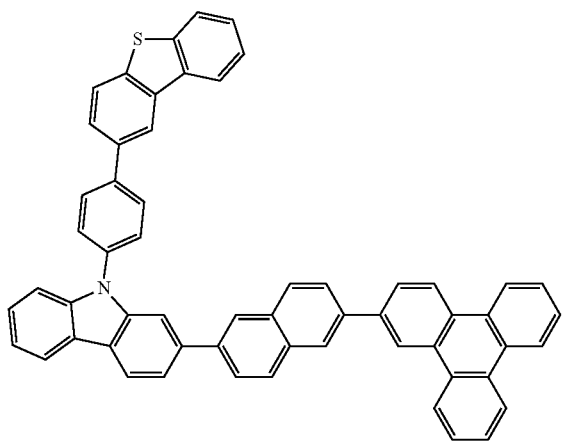

-continued
Chemical Formula 1-31
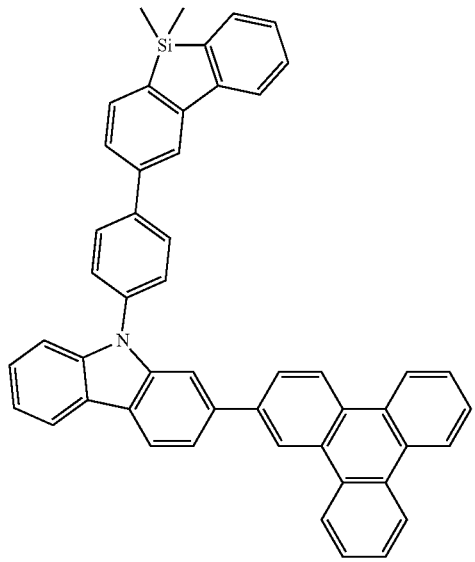
Chemical Formula 1-32
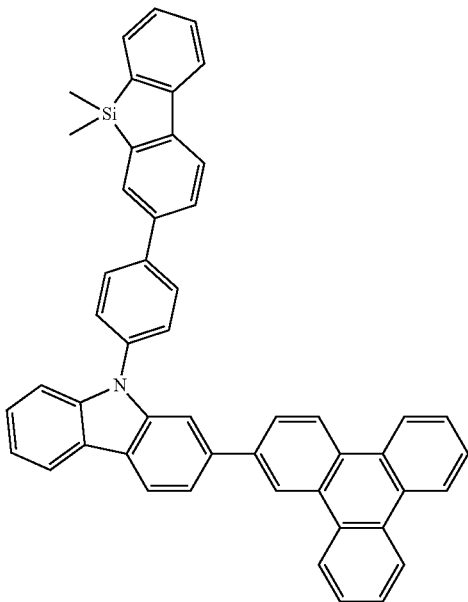
Chemical Formula 1-33
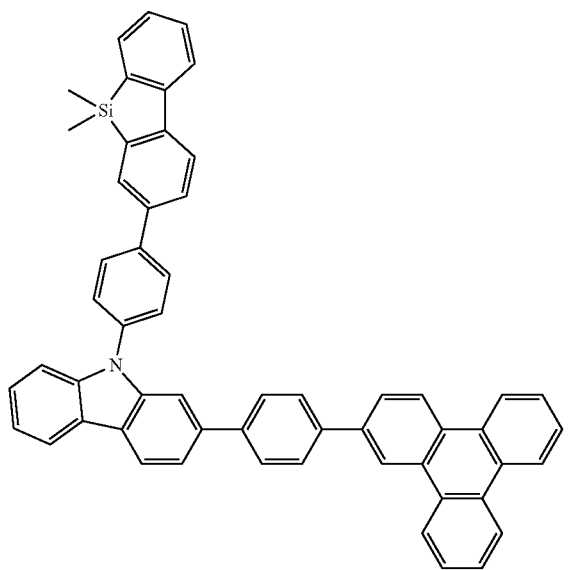
Chemical Formula 1-34
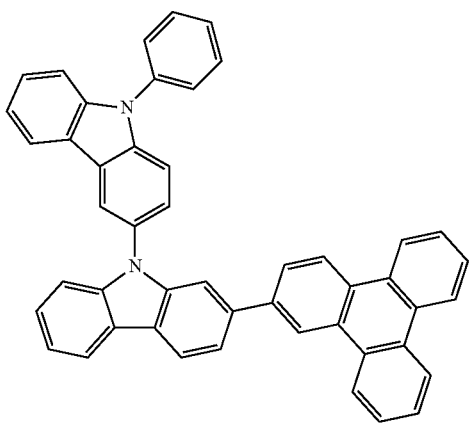

-continued
Chemical Formula 1-35
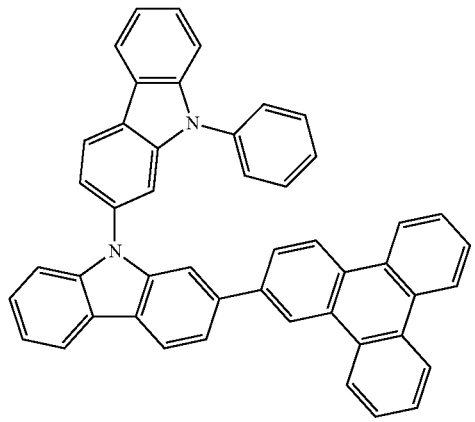
Chemical Formula 1-36
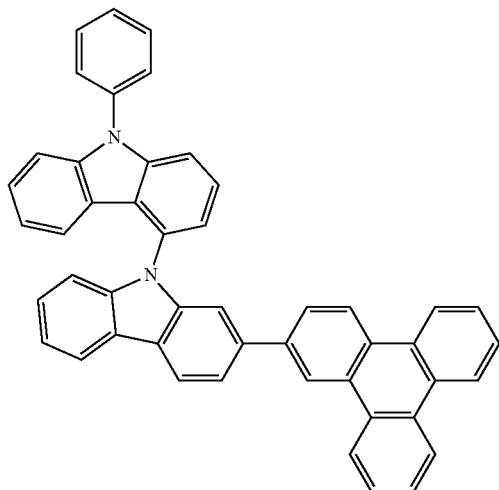
Chemical Formula 1-37
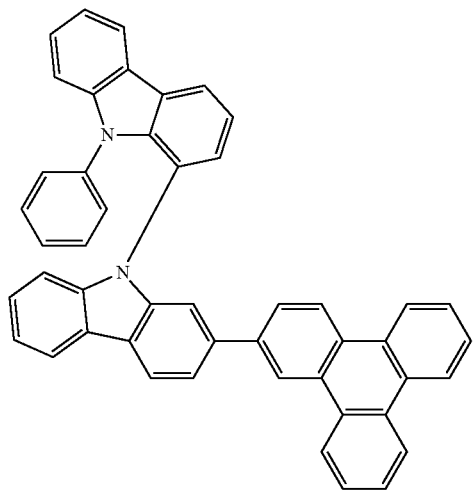
Chemical Formula 1-38
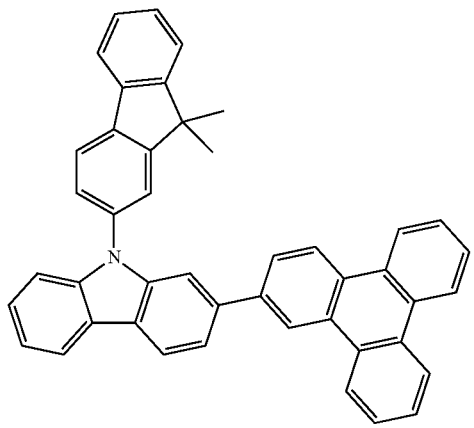
Chemical Formula 1-39
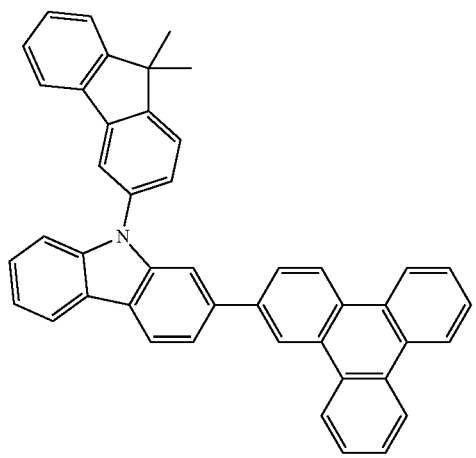
Chemical Formula 1-40
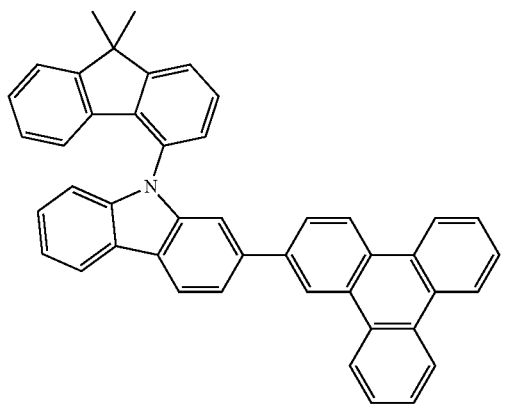

-continued
Chemical Formula 1-41
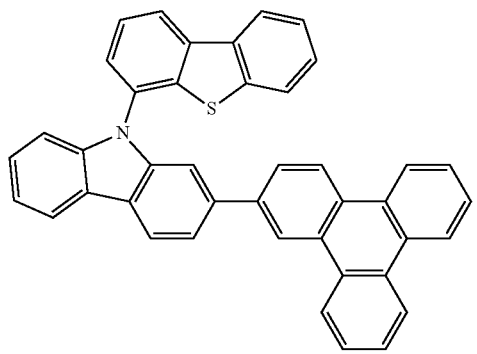
Chemical Formula 1-42
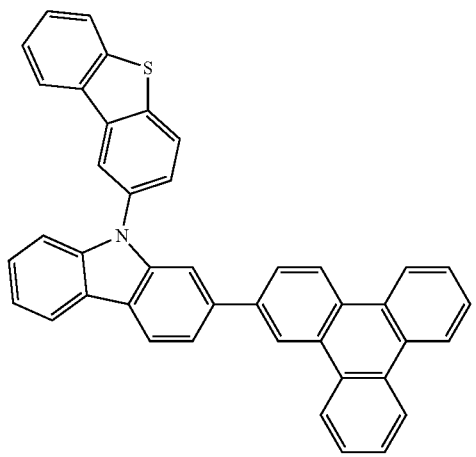
Chemical Formula 1-43
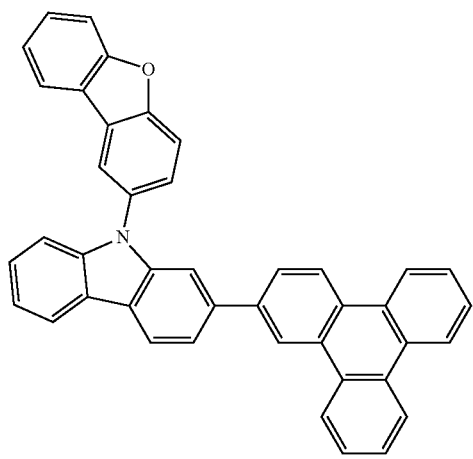
Chemical Formula 1-44
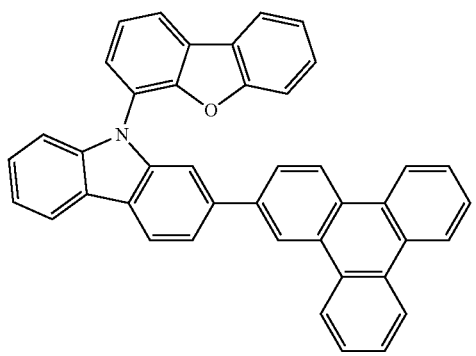
Chemical Formula 1-45
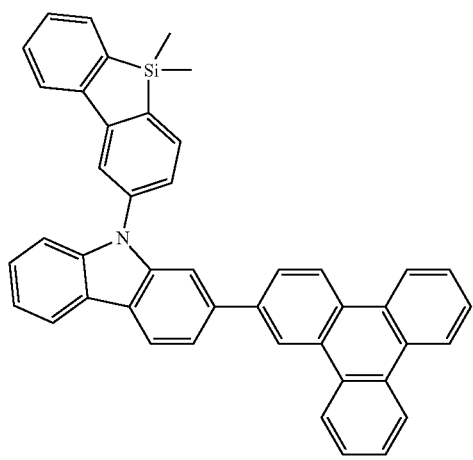
Chemical Formula 1-46
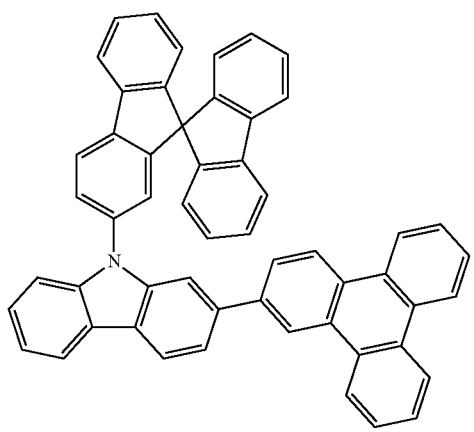

-continued
Chemical Formula 1-47
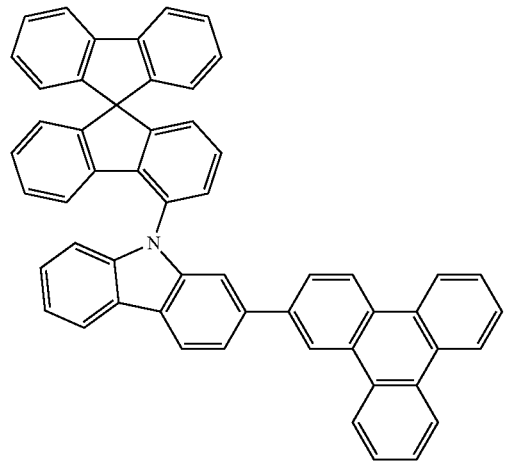
Chemical Formula 1-48
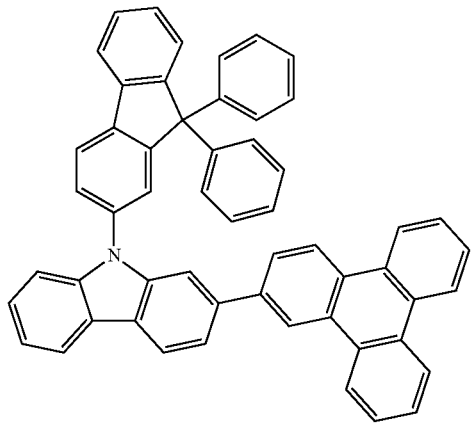
Chemical Formula 1-49
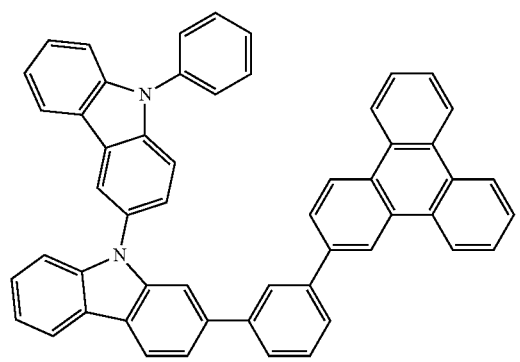
Chemical Formula 1-50
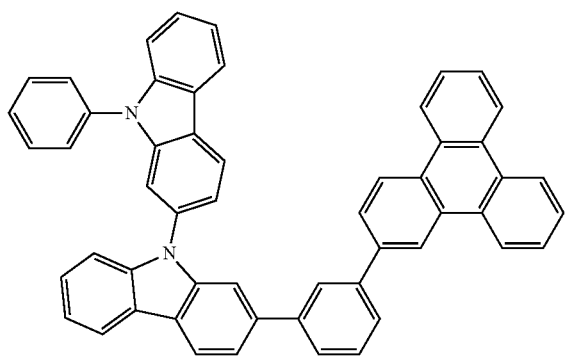
Chemical Formula 1-51
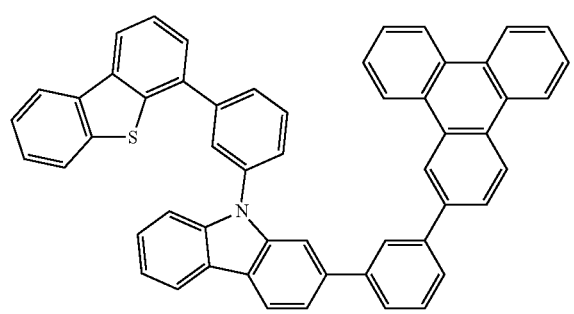
Chemical Formula 1-52
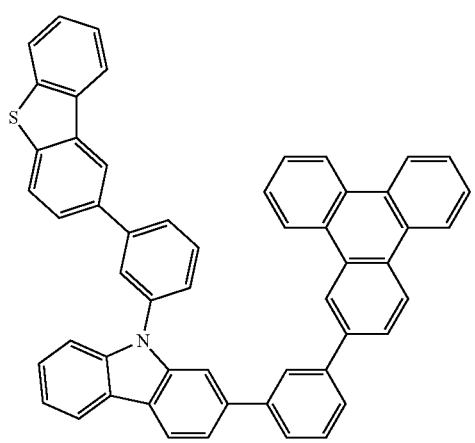

Chemical Formula 1-53
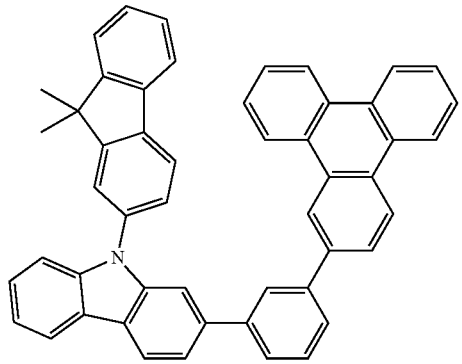
Chemical Formula 1-54
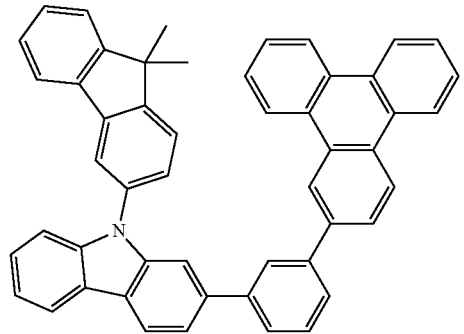
Chemical Formula 1-55
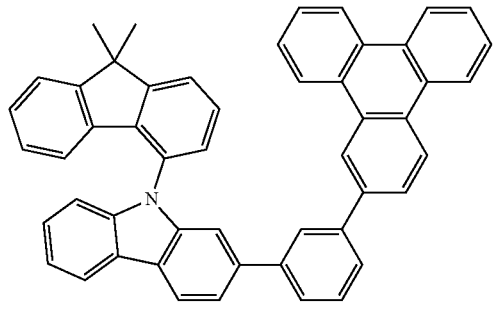
Chemical Formula 1-56
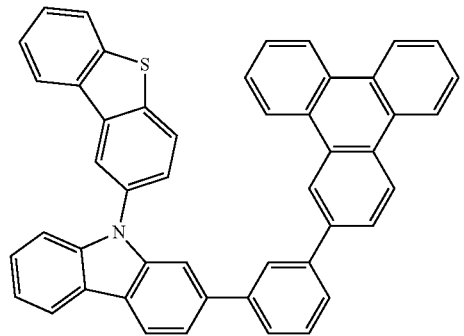
Chemical Formula 1-57
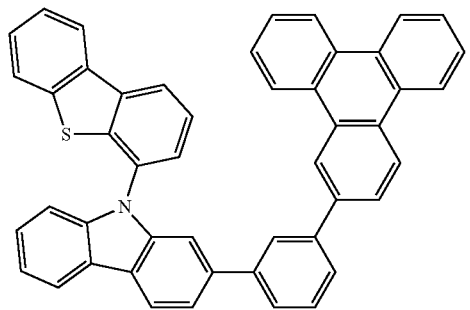
Chemical Formula 1-58
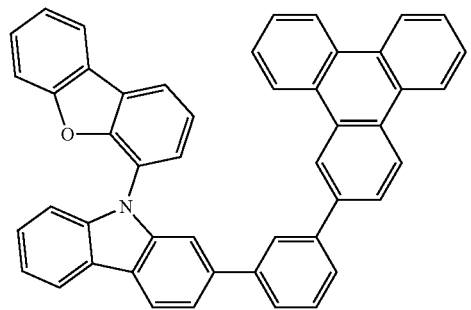
Chemical Formula 1-59
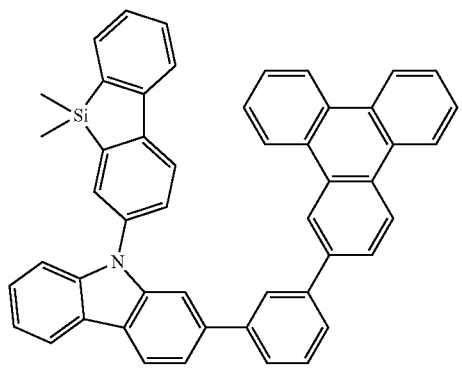
Chemical Formula 1-60
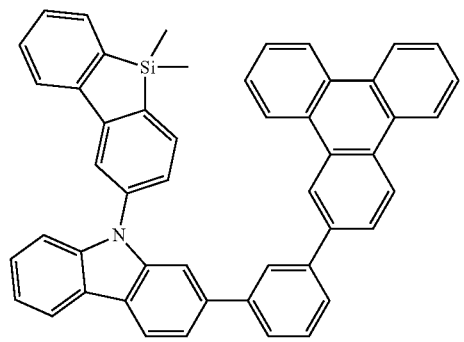

Chemical Formula 1-61
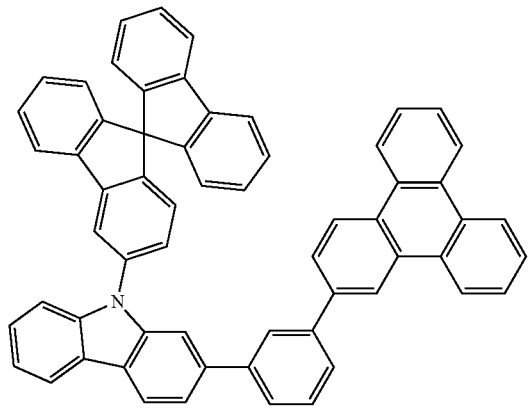
Chemical Formula 1-62
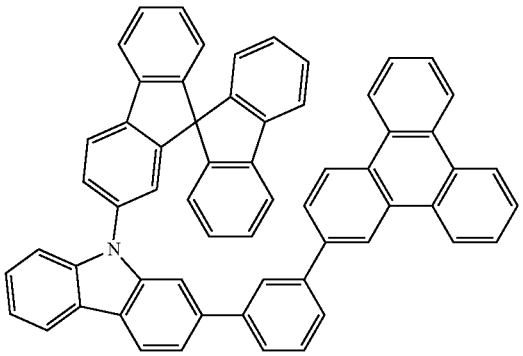
Chemical Formula 1-63
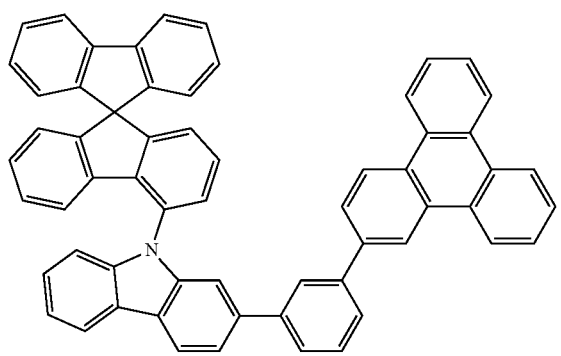
Chemical Formula 1-64
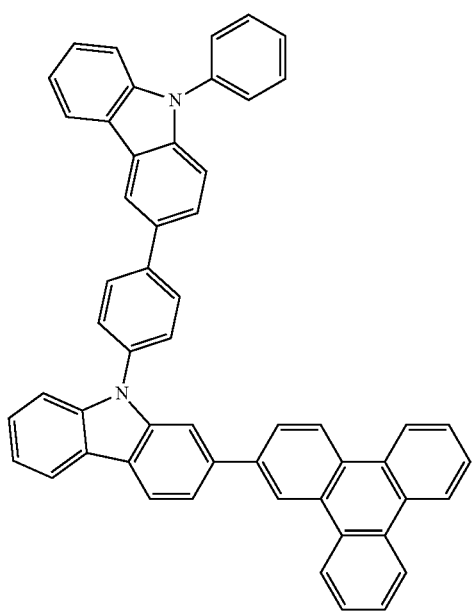
Chemical Formula 1-65
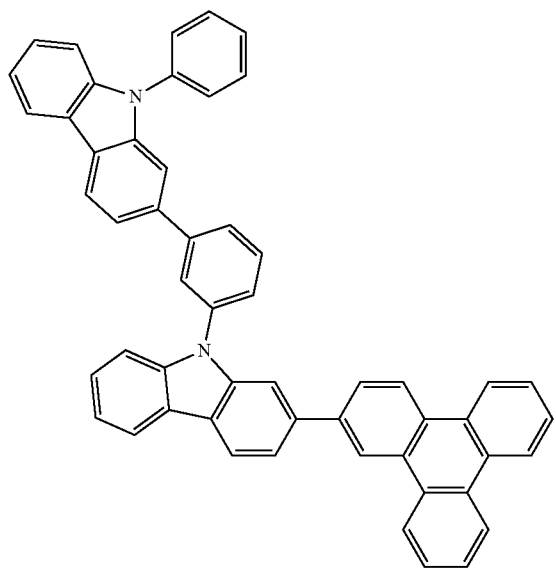
Chemical Formula 1-66
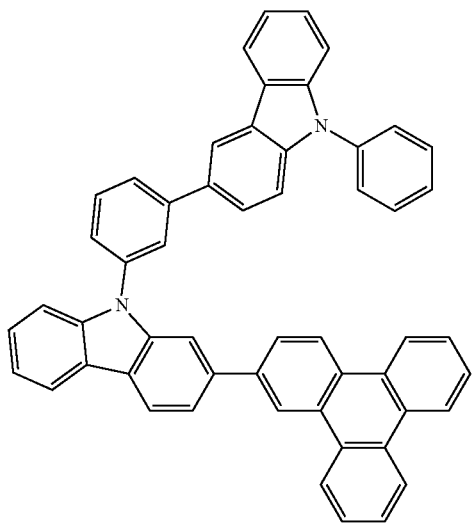

-continued
Chemical Formula 1-67
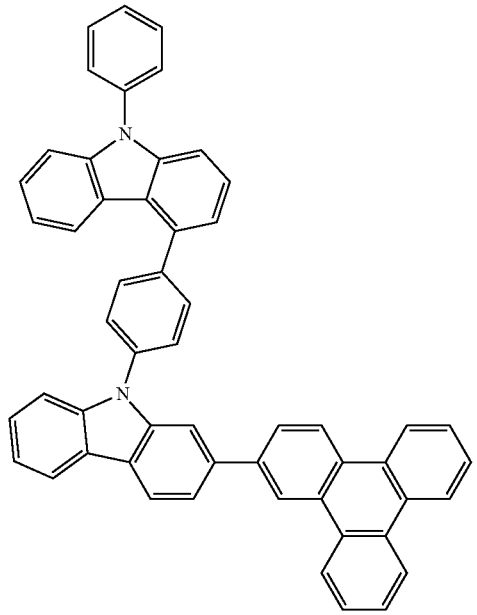
Chemical Formula 1-68
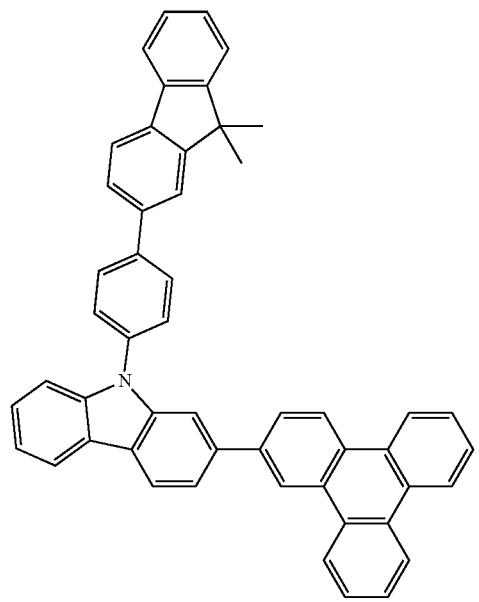
Chemical Formula 1-69
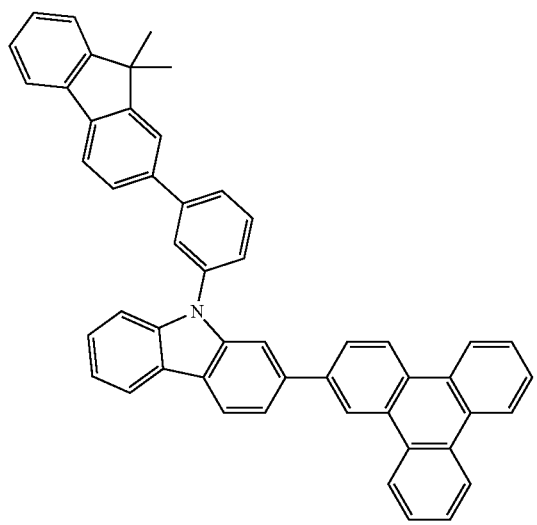
Chemical Formula 1-70
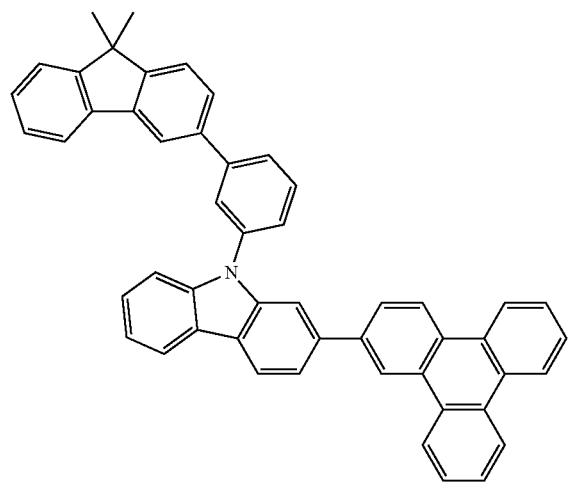
Chemical Formula 1-71
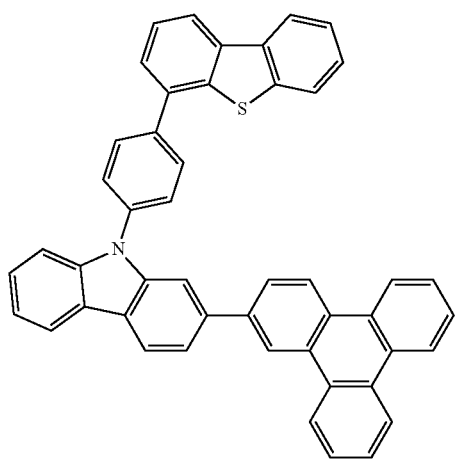
Chemical Formula 1-72
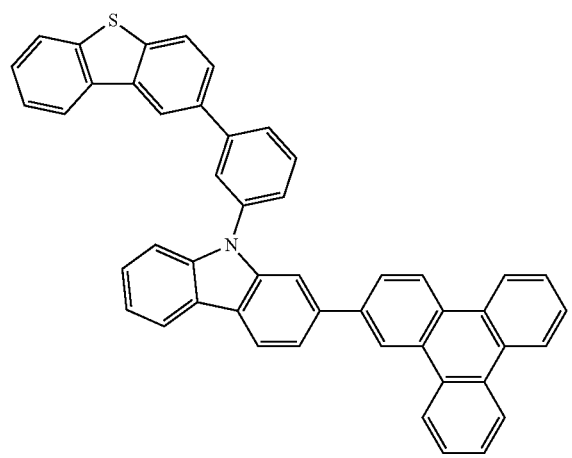

Chemical Formula 1-73
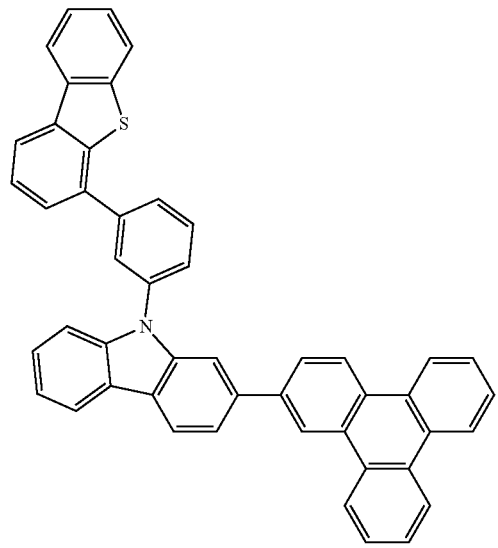
Chemical Formula 1-74
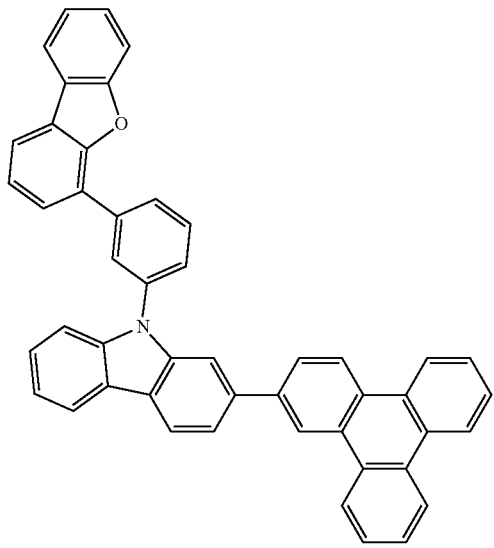
Chemical Formula 1-75
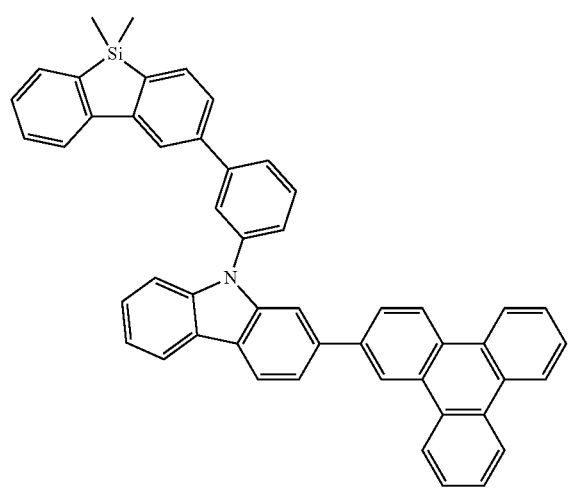
Chemical Formula 1-76
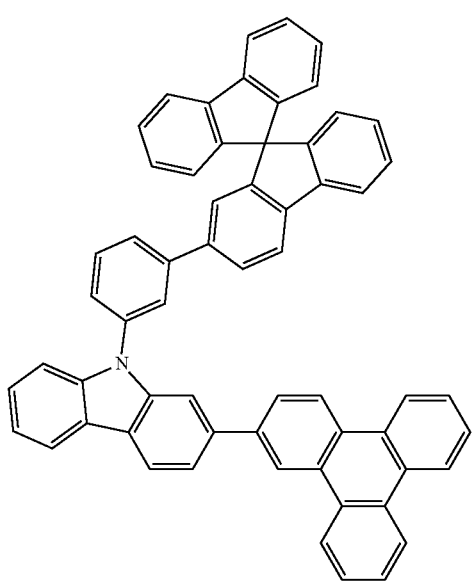

-continued
Chemical Formula 1-77
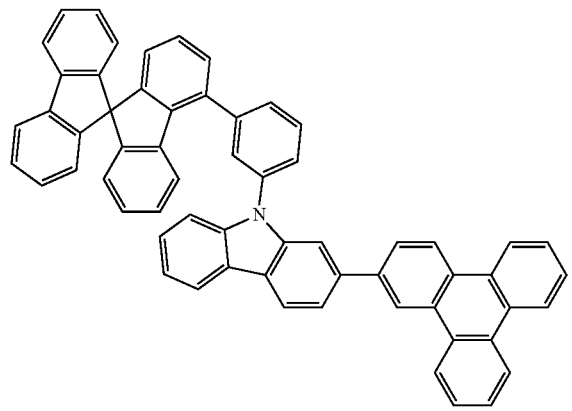
Chemical Formula 1-78
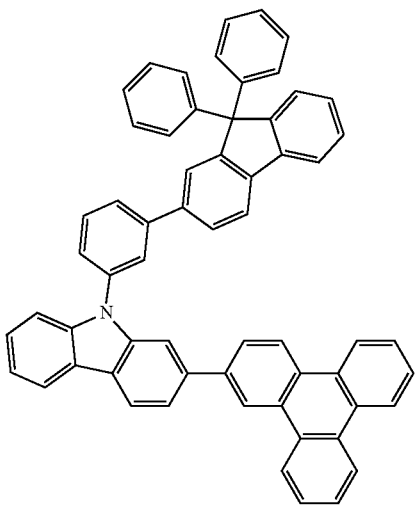
Chemical Formula 1-79
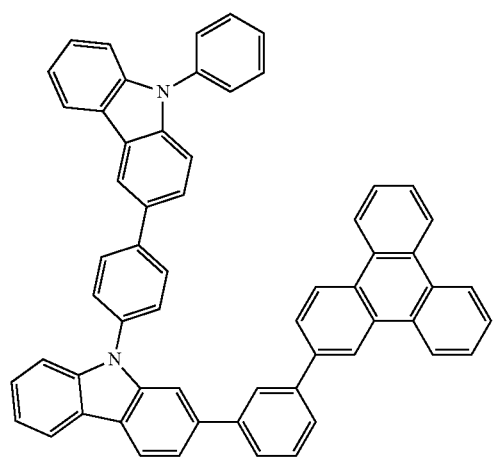
Chemical Formula 1-80
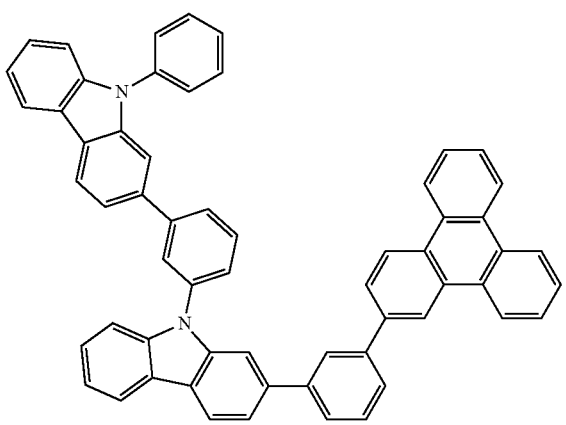
Chemical Formula 1-81
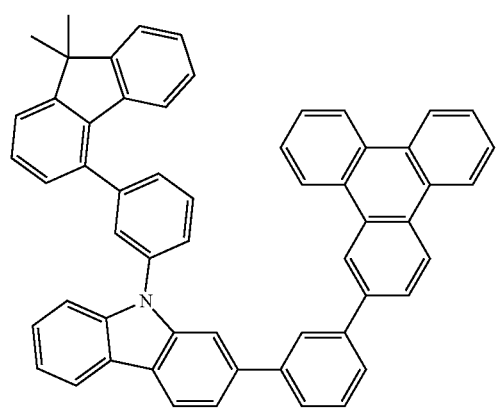
Chemical Formula 1-82
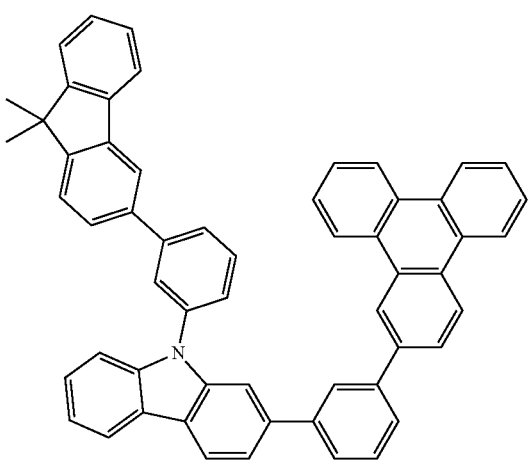

Chemical Formula 1-83
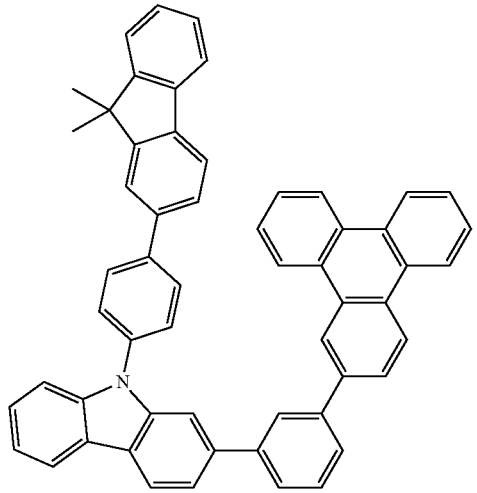
Chemical Formula 1-84
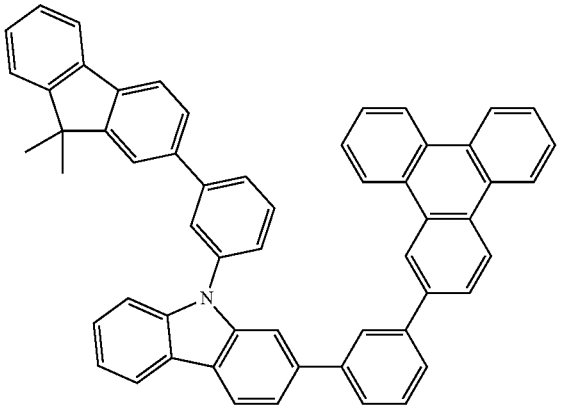
The compound represented by Chemical Formula 1 may be prepared based on preparation examples described later.
According to one embodiment, the compound represented by Chemical Formula 1 may be prepared in the same manner as in the following Reaction Formula 1.
[Reaction Formula 1]
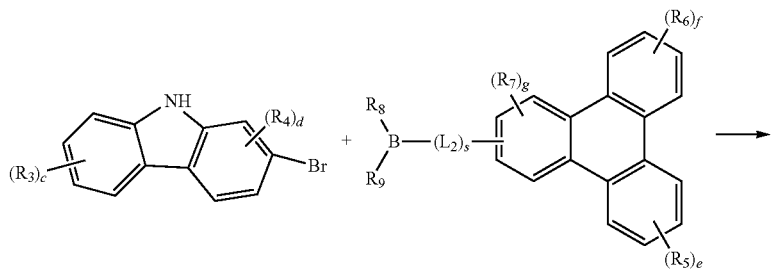
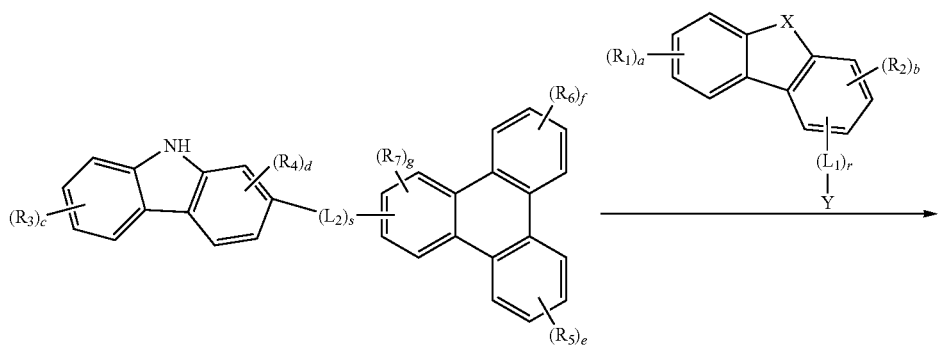

-continued

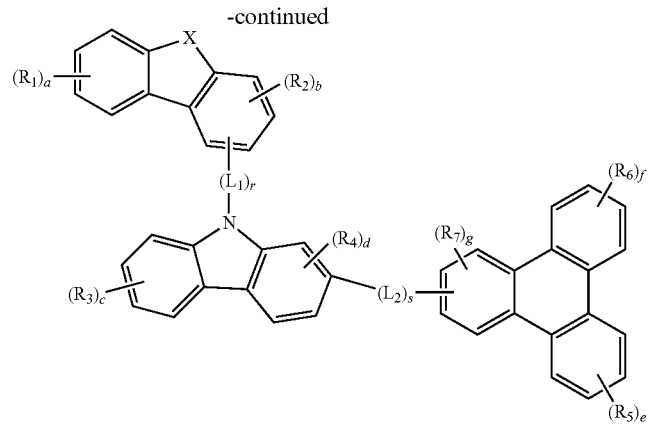

In Reaction Formula 1,
definitions of the substituents are the same as in Chemical Formula 1,
Y is Br or Cl, and
$R_8$ and $R_9$ are the same as or different from each other, and each independently —OH or —OC(CH$_3$)$_2$C(CH$_3$)$_2$O, the carbazole intermediate is synthesized through a Suzuki reaction, and the final compound is synthesized through a Buchwald-Hartwig reaction.

In addition, the present specification provides an organic light emitting device including the compound represented by Chemical Formula 1.

One embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present specification may be formed in a monolayer structure, but may also be formed in a multilayer structure in which two or more organic material layers are laminated. For example, the organic light emitting device of the present invention may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In one embodiment of the present specification, the organic material layer includes a hole injection layer, a hole transfer layer or a layer carrying out hole injection and transfer at the same time, and the hole injection layer, the hole transfer layer, or the layer carrying out hole injection and transfer at the same time includes the compound of Chemical Formula 1.

In another embodiment, the organic material layer includes a light emitting layer, and the light emitting layer includes the compound of Chemical Formula 1.

In one embodiment of the present specification, the organic material layer includes an electron transfer layer or an electron injection layer, and the electron transfer layer or the electron injection layer includes the compound of Chemical Formula 1.

In one embodiment of the present specification, the electron transfer layer, the electron injection layer or the layer carrying out electron transfer and electron injection at the same time includes the compound of Chemical Formula 1.

In another embodiment, the organic material layer includes a light emitting layer and an electron transfer layer, and the electron transfer layer includes the compound of Chemical Formula 1.

In another embodiment, the organic light emitting device may be an organic light emitting device having a normal-type structure in which an anode, one or more organic material layers and a cathode are laminated in consecutive order on a substrate.

In another embodiment, the organic light emitting device may be an organic light emitting device having an inverted-type structure in which a cathode, one or more organic material layers and an anode are laminated in consecutive order on a substrate.

For example, the structures of an organic light emitting device according to one embodiment of the present specification are illustrated in FIGS. 1 and 2.

FIG. 1 is a diagram showing an example of an organic light emitting device formed with a substrate (1), an anode (2), a light emitting layer (3) and a cathode (4). In such a structure, the compound may be included in the light emitting layer.

FIG. 2 is a diagram showing an example of an organic light emitting device formed with a substrate (1), an anode (2), a hole injection layer (5), a hole transfer layer (6), a light emitting layer (7), an electron transfer layer (8) and a cathode (4). In such a structure, the compound may be included in one or more layers of the hole injection layer, the hole transfer layer, the light emitting layer and the electron transfer layer.

The organic light emitting device of the present specification may be manufactured using materials and methods known in the art, except that one or more layers of organic material layers include the compound of the present specification, that is, the compound of Chemical Formula 1.

When the organic light emitting device includes a plurality of organic material layers, the organic material layers may be formed with the same material or with different materials.

For example, the organic light emitting device of the present specification may be manufactured by consecutively laminating a first electrode, an organic material layer and a second electrode on a substrate. Herein, the organic light emitting device may be manufactured by forming an anode on the substrate by depositing a metal, a metal oxide having conductivity, or alloys thereof using a physical vapor deposition (PVD) method such as a sputtering method or an e-beam evaporation method, forming the organic material layer including a hole injection layer, a hole transfer layer, a light emitting layer and an electron transfer layer thereon, and then depositing a material capable of being used as a cathode thereon.—

In addition, the compound of Chemical Formula 1 may be formed as the organic material layer using a solution coating method as well as a vacuum deposition method when manufacturing the organic light emitting device. Herein, the solution coating method means spin coating, dip coating, doctor blading, ink jet printing, screen printing, a spray method, roll coating and the like, but is not limited thereto.

In addition to this method, the organic light emitting device may also be manufactured by consecutively depositing a cathode material, an organic material layer and an anode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the anode material, a material having large work function is normally preferable so that hole injection to the organic material layer is smooth. Specific examples of the anode material capable of being used in the present invention include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylen-1,2-dioxy)thiophene] (PEDOT), polypyrrole and polyaniline, and the like, but are not limited thereto.

As the cathode material, a material having small work function is normally preferable so that electron injection to the organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include a metal porphyrin, oligothiophene, an arylamine-based organic material, a hexanitrile hexazatriphenylene-based organic material, a quinacridone-based organic material, a perylene-based organic material, anthraquinone, and a polyaniline- and a polythiophene-based conductive polymer, and the like, but are not limited thereto.

The hole transfer layer is a layer that receives holes from a hole injection layer and transfers the holes to a light emitting layer, and as the hole transfer material, a material capable of receiving holes from an anode or a hole injection layer, moving the holes to a light emitting layer, and having high mobility for the holes, is suitable. Specific examples thereof include an arylamine-based organic material, a conductive polymer, a block copolymer having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly(p-phenylenevinylene) (PPV)-based polymer; a spiro compound; polyfluorene, rubrene, and the like, but are not limited thereto.

The light emitting layer may include a host material and a dopant material. The host material includes a fused aromatic ring derivative, a heteroring-containing compound or the like. Specifically, the fused aromatic ring derivative includes an anthracene derivative, a pyrene derivative, a naphthalene derivative, a pentacene derivative, a phenanthrene compound, a fluoranthene compound and the like, and the heteroring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex and the like. Specifically, the aromatic amine derivative is a fused aromatic ring derivative having a substituted or unsubstituted arylamino group and includes arylamino group-including pyrene, anthracene, crycene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of favorably receiving electrons from a cathode, moving the electrons to a light emitting layer, and having high mobility for the electrons, is suitable. Specific examples thereof include an Al complex of 8-hydroxyquinoline; a complex including $Alq_3$; an organic radical compound; a hydroxyflavon-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The organic light emitting device according to the present specification may be a top-emission type, a bottom-emission type or a dual-emission type depending on the materials used.

In one embodiment of the present specification, the compound of Chemical Formula 1 may be included in an organic solar cell or an organic transistor in addition to an organic light emitting device.

The preparation of the compound represented by Chemical Formula 1 and the organic light emitting device including the compound will be described in detail in the following examples. However, the following examples are for illustrative purposes only, and the scope of the present specification is not limited thereto.

<Preparation Example 1> Preparation of Compound P1

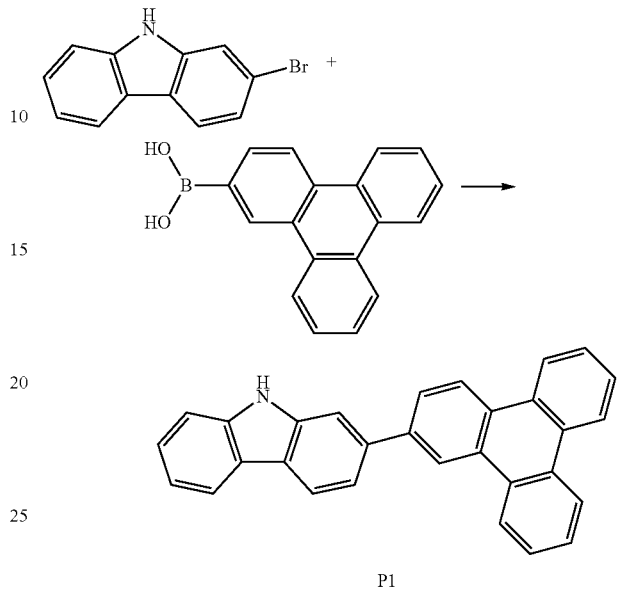

P1

2-Bromocarbazole (10.0 g, 40.6 mmol), triphenylene-2-boronic acid (13.2 g, 48.5 mmol) and potassium carbonate (17.0 g, 123 mmol) were suspended in a mixture of tetrahydrofuran (100 mL) and water (50 mL). After nitrogen packing, tetrakis(triphenylphosphine)palladium (0.9 g, 0.7 mmol) was added to the suspension. Under nitrogen, the mixture was stirred for approximately 12 hours under reflux. After the result was cooled to room temperature, the produced solids were filtered. The light yellow solids were purified using THF/EtOH to obtain white solid P1 (13 g, 81%).

MS [M+H]: 394

<Preparation Example 2> Preparation of Compound P2

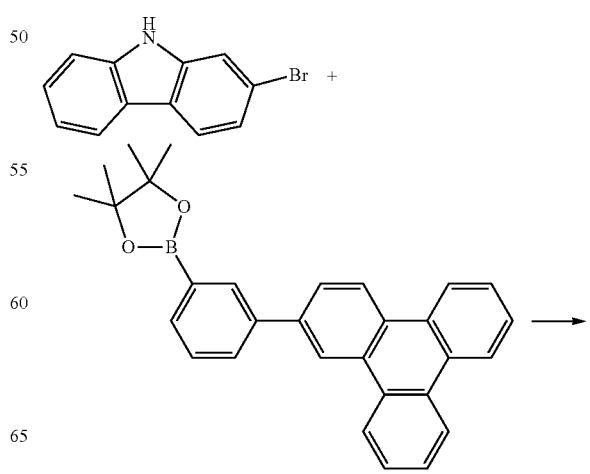

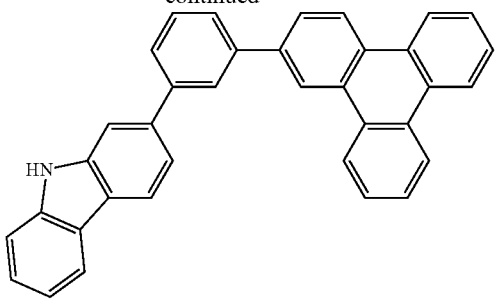

P2

White compound P2 (88%) was obtained in the same manner as in Preparation Example 1 except that compound P2 was used instead of compound P1.

MS [M+H]: 470

<Preparation Example 3> Preparation of Compound P4

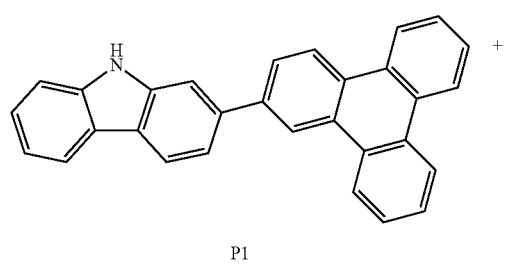

P1

+

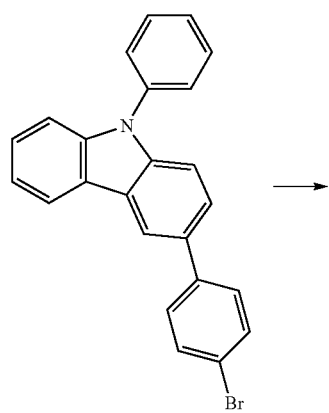

→

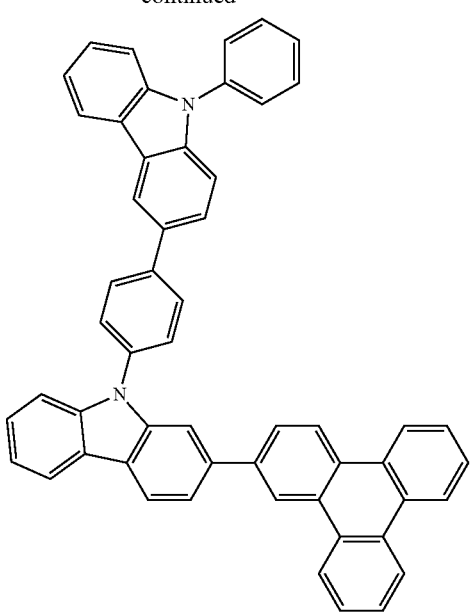

1-1

Compound P1 (8.2 g, 20.8 mmol), 3-(4-bromophenyl)-9-phenyl-9H-carbazole (8.2 g, 20.5 mmol), bis(tritertiary-butylphosphine)palladium (0.1 g, 0.2 mmol) and sodium tertiary-butoxide (2.8 g, 29.1 mmol) were mixed, and the result was refluxed while being stirred for 4 hours in xylene (50 ml) under nitrogen. The temperature was lowered to room temperature and the solvent was removed under vacuum. Light yellow solids were dissolved in chloroform, the result was stirred after adding magnesium sulfate and acid clay thereto, and the result was filtered and vacuum distilled. The result was recrystallized using chloroform and ethyl acetate to obtain Chemical Formula 1-1 (9.9 g, 67%), a white solid compound.

MS [M+H]: 711

Compounds listed in the table below were each prepared according to the preparation method of Chemical Formula 1-1 of <Preparation Example 3>. The structures, forms, yields and MS were summarized in Table 1 below.

TABLE 1

| Preparation Example | Intermediate 1 (Px) | Intermediate 2 | Chemical Formula | Form | Yield (%) | MS [M + H] |
|---|---|---|---|---|---|---|
| Preparation Example 5 Chemical Formula 1-2 | P1 | | | White Solid | 77 | 635 |
| Preparation Example 6 Chemical Formula 1-3 | P2 | | | White Solid | 80 | 787 |

TABLE 1-continued
| | Intermediate 1 (Px) | Intermediate 2 | Chemical Formula | Form | Yield (%) | MS [M + H] |
|---|---|---|---|---|---|---|
| Preparation Example 7 Chemical Formula 1-14 | P1 | 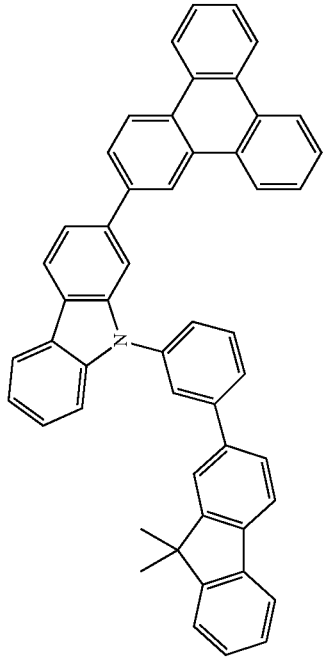 | 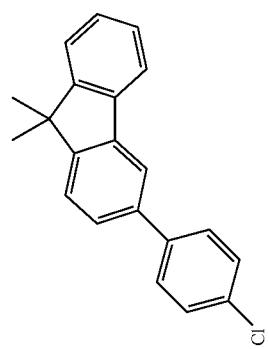 | White Solid | 67 | 662 |
| Preparation Example 8 Chemical Formula 1-19 | P1 | | | White Solid | 81 | 662 |

TABLE 1-continued
| Preparation Example | Intermediate 1 (Px) | Intermediate 2 | Chemical Formula | Form | Yield (%) | MS [M + H] |
|---|---|---|---|---|---|---|
| Preparation Example 9 Chemical Formula 1-26 | P1 | 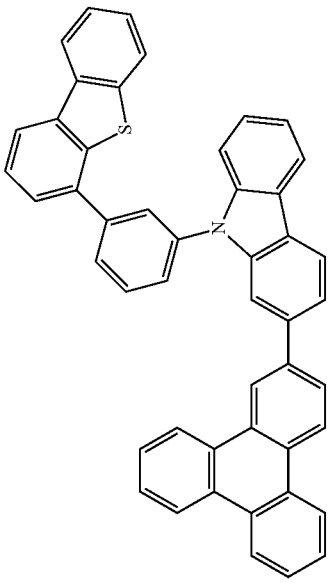 | | White Solid | 67 | 652 |

Example 1

A glass substrate on which indium tin oxide (ITO) was coated as a thin film to a thickness of 1,500 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed to a thickness of 500 Å by thermal vacuum depositing hexanitrile hexaazatriphenylene (HAT) of the following Chemical Formula.

[HAT]

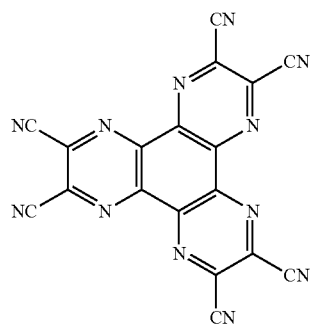 [SMILES: N#Cc1nc2c3nc(C#N)c(C#N)nc3c3nc(C#N)c(C#N)nc3c2nc1C#N]

A hole transfer layer was formed on the hole injection layer to a thickness of 400 Å by thermal vacuum depositing an N,N-bis-(1-naphthalenyl)-N,N-bis-phenyl-(1,1-biphenyl)-4,4-diamine (NPB) compound of the following structure.

[NPB]

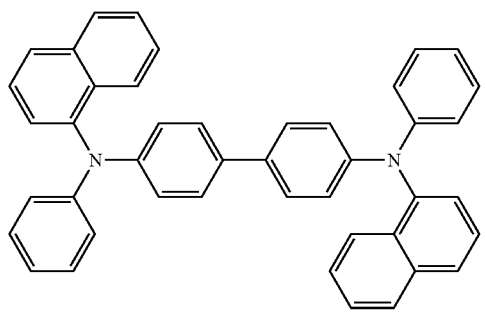 [SMILES: c1ccc(N(c2ccc(-c3ccc(N(c4ccccc4)c4cccc5ccccc45)cc3)cc2)c2cccc3ccccc23)cc1]

Subsequently, a light emitting layer was formed on the hole transfer layer to a film thickness of 300 Å by vacuum depositing the compound of Chemical Formula 1-1 prepared in Preparation Example 1 with an Ir(ppy)$_3$ dopant in a 10% concentration.

An electron injection and transfer layer was formed on the light emitting layer to a thickness of 200 Å by vacuum depositing an electron transfer material such as below.

[Electron Transfer Material]

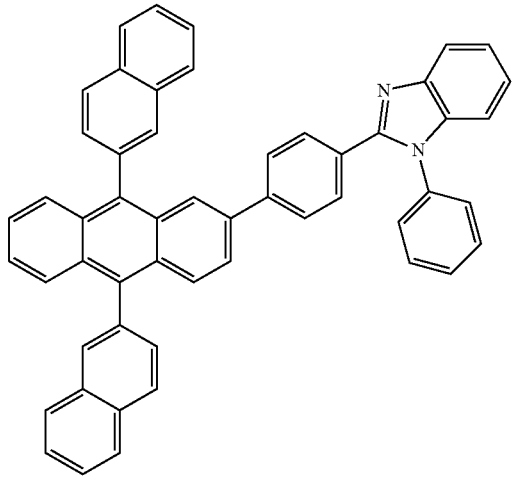 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

A cathode was formed on the electron injection and transfer layer by depositing lithium fluoride (LiF) to a thickness of 12 Å and aluminum to a thickness of 2,000 Å in consecutive order.

In the above-mentioned process, the deposition rates of the organic materials were maintained at 0.4 to 0.7 Å/sec, the deposition rates of the lithium fluoride and the aluminum of the cathode were maintained at 0.3 Å/sec and 2 Å/sec, respectively, and the degree of vacuum when being deposited was maintained at $2 \times 10^{-7}$ to $5 \times 10^{-8}$ torr.

Example 2

An organic light emitting device was manufactured in the same manner as in Example 1 except that the compound of Chemical Formula 1-2 was used instead of the compound of Chemical Formula 1-1.

Example 3

An organic light emitting device was manufactured in the same manner as in Example 1 except that the compound of Chemical Formula 1-3 was used instead of the compound of Chemical Formula 1-1.

Example 4

An organic light emitting device was manufactured in the same manner as in Example 1 except that the compound of Chemical Formula 1-14 was used instead of the compound of Chemical Formula 1-1.

Example 5

An organic light emitting device was manufactured in the same manner as in Example 1 except that the compound of Chemical Formula 1-19 was used instead of the compound of Chemical Formula 1-1.

Example 6

An organic light emitting device was manufactured in the same manner as in Example 1 except that the compound of Chemical Formula 1-26 was used instead of the compound of Chemical Formula 1-1.

Comparative Example 1

An organic light emitting device was manufactured in the same manner as in Example 1 except that the following H1 was used instead of the compound of Chemical Formula 1-1.

H1

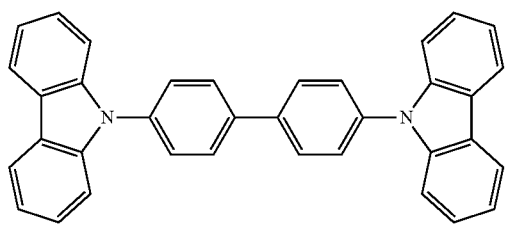

Comparative Example 2

An organic light emitting device was manufactured in the same manner as in Example 1 except that the following H2 was used instead of the compound of Chemical Formula 1-1.

H2

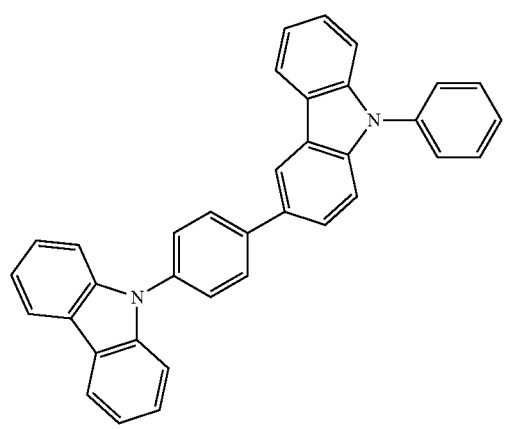

Comparative Example 3

An organic light emitting device was manufactured in the same manner as in Example 1 except that the following H3 was used instead of the compound of Chemical Formula 1-1.

H3

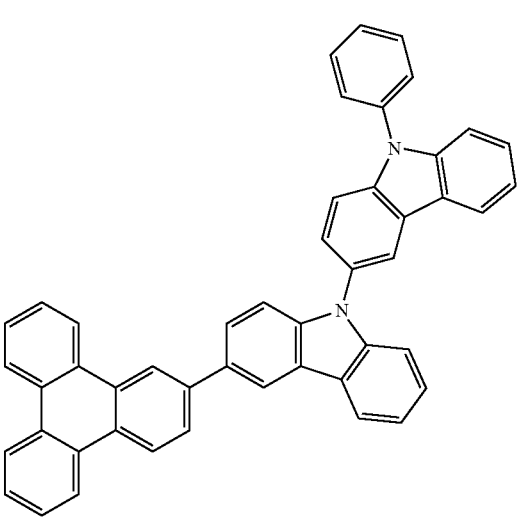

The results of devices manufactured using each compound of Examples 1 to 6 and Comparative Examples 1 to 3 as the light emitting layer are shown in Table 2.

TABLE 2

| No. | Host | Dopant | Doping Concentration (%) | Driving Voltage (V) @5,000 cd/m$^2$ | Light Emission Efficiency (Cd/A) | Relative Lifespan ($T_{95\%}$) |
|---|---|---|---|---|---|---|
| Comparative Example 1 | H1 | Ir(ppy)$_3$ | 10 | 5.2 | 32 | 1 |
| Comparative Example 2 | H2 | Ir(ppy)$_3$ | 10 | 5.1 | 28 | 0.8 |
| Comparative Example 3 | H3 | Ir(ppy)$_3$ | 10 | 5.0 | 36 | 1.8 |
| Example 1 | Chemical Formula 1-1 | Ir(ppy)$_3$ | 10 | 4.8 | 40 | 2.3 |
| Example 2 | Chemical Formula 1-2 | Ir(ppy)$_3$ | 10 | 4.9 | 36 | 2.1 |
| Example 3 | Chemical Formula 1-3 | Ir(ppy)$_3$ | 10 | 4.5 | 34 | 2.1 |
| Example 4 | Chemical Formula 1-14 | Ir(ppy)$_3$ | 10 | 4.2 | 38 | 3.9 |
| Example 5 | Chemical Formula 1-19 | Ir(ppy)$_3$ | 10 | 4.3 | 44 | 2.5 |
| Example 6 | Chemical Formula 1-26 | Ir(ppy)$_3$ | 10 | 4.6 | 40 | 2.1 |

As identified in Table 1, the compounds of the present specification in Examples 1 to 6 are capable of being used as a host of a green light emitting layer, and exhibit more enhanced efficiency and a longer lifespan compared to the compounds in Comparative Examples 1 to 3.

Compounds described in the present specification can be used as a material of an organic material layer of an organic light emitting device. Compounds according to at least one embodiment are capable of efficiency enhancement, a low driving voltage and/or lifespan property enhancement in an organic light emitting device. In particular, compounds described in the present specification can be used as a material of hole injection, hole transfer, hole injection and transfer, light emission, electron transfer, or electron injection.

What is claimed is:

1. A compound represented by the following Chemical Formula 1:

[Chemical Formula 1]

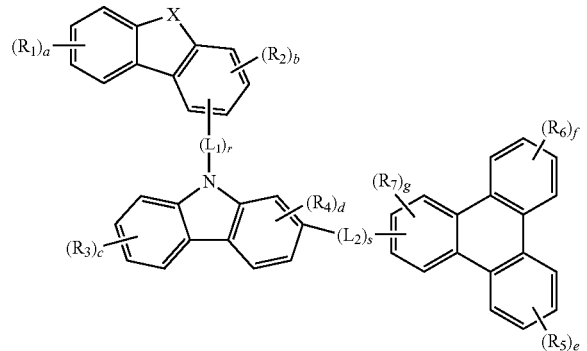

wherein, in Chemical Formula 1,

X is O, S, NAr, $CR_{11}R_{12}$, or $SiR_{13}R_{14}$, $L_1$ and $L_2$ are the same as or different from each other, and each independently a direct bond, substituted or unsubstituted arylene, or substituted or unsubstituted heteroarylene including one or more of O and S atoms, $R_1$ to $R_4$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted hetero-cyclic group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, $R_5$ to $R_7$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted hetero-cyclic group; or a substituted or unsubstituted alkylamine group, or adjacent two or more substituents bond to each other to form a substituted or unsubstituted hydrocarbon ring or heteroring, Ar is a substituted or unsubstituted aryl group or heteroaryl group, $R_{11}$, $R_{12}$, $R_{13}$ and $R_{14}$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; or a substituted or unsubstituted hetero-cyclic group, or $R_{11}$ and $R_{12}$ or $R_{13}$ and $R_{14}$ bond to each other to form a substituted or unsubstituted hydrocarbon ring or a substituted or unsubstituted heteroring, a, c, e and f are the same as or different from each other, and each independently an integer of 0 to 4, b, d and g are the same as or different from each other, and each independently an integer of 0 to 3, r and s are the same as or different from each other, and each independently an integer of 1 to 3, when a is two or greater, $R_1$s are the same as or different from each other, when b is two or greater, $R_2$s are the same as or different from each other, when c is two or greater, $R_3$s are the same as or different from each other, when d is two or greater, $R_4$s are the same as or different from each other, when e is two or greater, $R_5$s are the same as or different from each other, when f is two or greater, $R_6$s are the same as or different from each other, when g is two or greater, $R_7$s are the same as or different from each other, when r is two or greater, $L_1$s are the same as or different from each other, and when s is two or greater, $L_2$s are the same as or different from each other;

with the proviso that when r=1, L1 is a phenylene group and X is NAr, Ar as a phenyl group is excluded.

2. The compound of claim 1, wherein Chemical Formula 1 is represented by any one of the following Chemical Formulae 2 to 4:

[Chemical Formula 2]

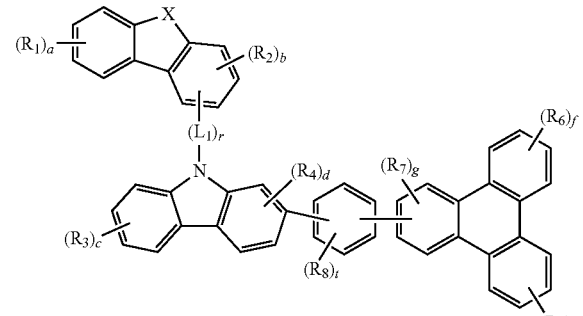

[Chemical Formula 3]

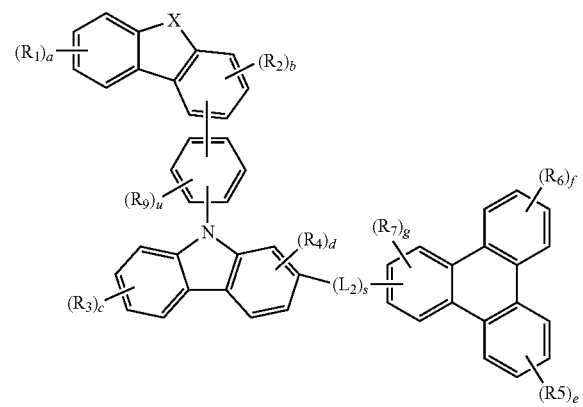

[Chemical Formula 4]

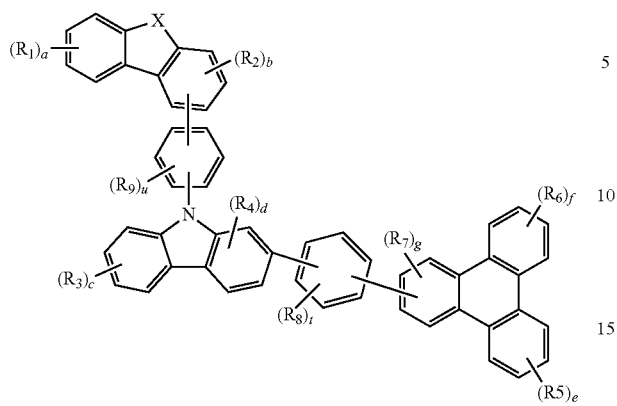

wherein, in Chemical Formulae 2 to 4, definitions of X, $R_1$ to $R_7$, $L_1$, $L_2$, a, b, c, d, e, f, g, r and s are the same as in Chemical Formula 1, $R_8$ and $R_9$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted hetero-cyclic group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or a substituted or unsubstituted heteroring, t and u are the same as or different from each other, and are each an integer of 0 to 4, when t is two or greater, $R_8$s are the same as or different from each other, and when u is two or greater, $R_9$s are the same as or different from each other.

3. The compound of claim 1, wherein Chemical Formula 1 is represented by any one of the following Chemical Formulae 5 to 9:

[Chemical Formula 5]

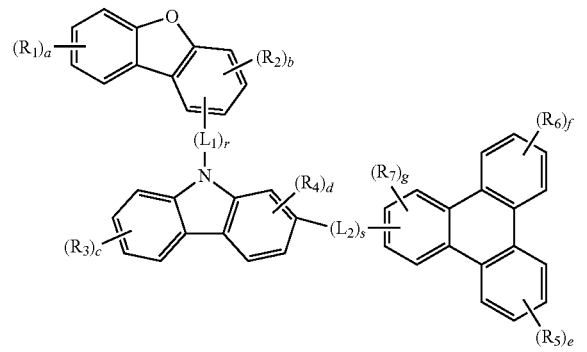

[Chemical Formula 6]

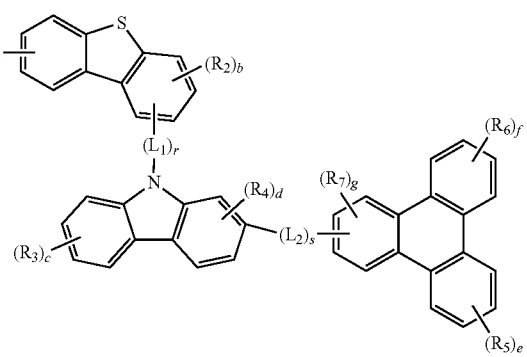

[Chemical Formula 7]

[Chemical Formula 8]

[Chemical Formula 9]

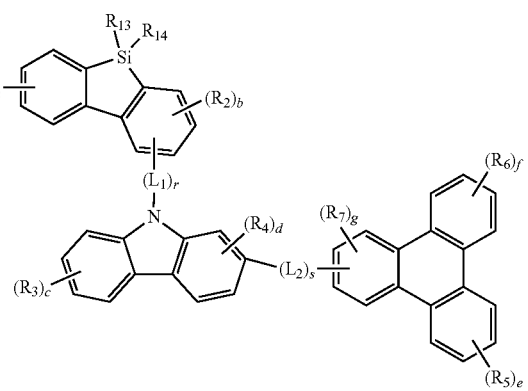

wherein, in Chemical Formulae 5 to 9,
definitions of $R_1$ to $R_7$, $L_1$, $L_2$, Ar, $R_{11}$ to $R_{14}$, a, b, c, d, e, f, g, r and s are the same as in Chemical Formula 1.

4. The compound of claim 1, wherein $L_1$ and $L_2$ are the same as or different from each other, and are a direct bond, or substituted or unsubstituted arylene.

5. The compound of claim 1, wherein $R_{11}$ and $R_{12}$ are the same as or different from each other, and each independently hydrogen; a substituted or unsubstituted alkyl group; or a substituted or unsubstituted aryl group, or bond to each other to form a fluorenyl group.

6. The compound of claim 1, wherein $R_{13}$ and $R_{14}$ are the same as or different from each other, and each independently hydrogen; a substituted or unsubstituted alkyl group; or a substituted or unsubstituted aryl group, or bond to each other to form a fluorenyl group.

7. The compound of claim 1, wherein the compound of Chemical Formula 1 is selected from the following Chemical Formulae:

Chemical Formula 1-2

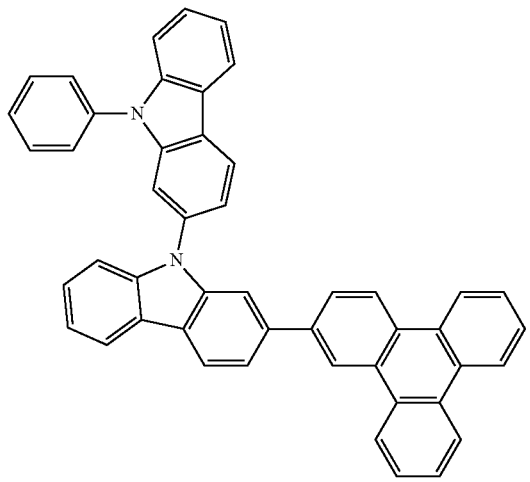

Chemical Formula 1-3

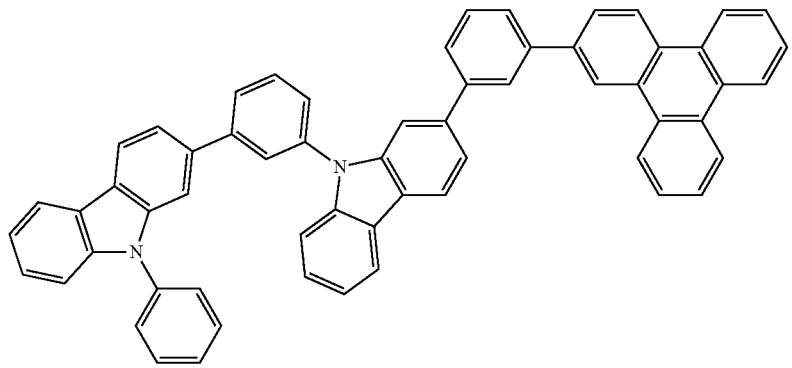

Chemical Formula 1-4

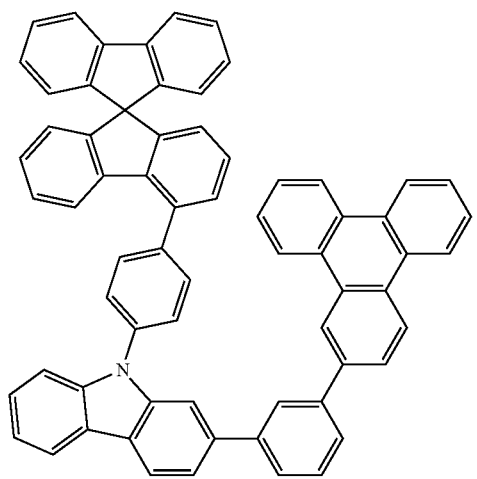

Chemical Formula 1-5

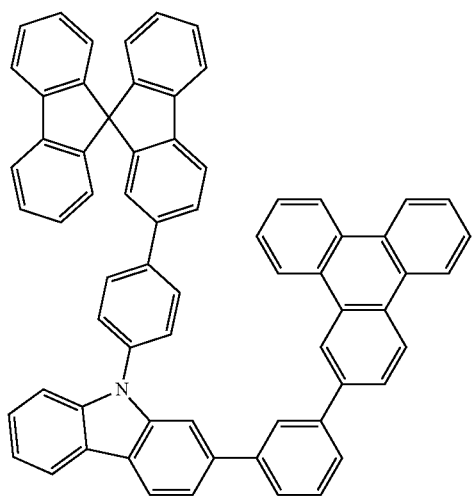

-continued
Chemical Formula 1-6
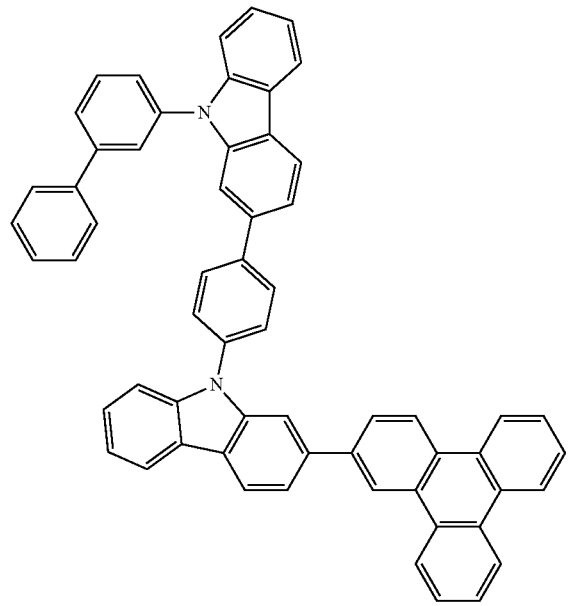
Chemical Formula 1-7
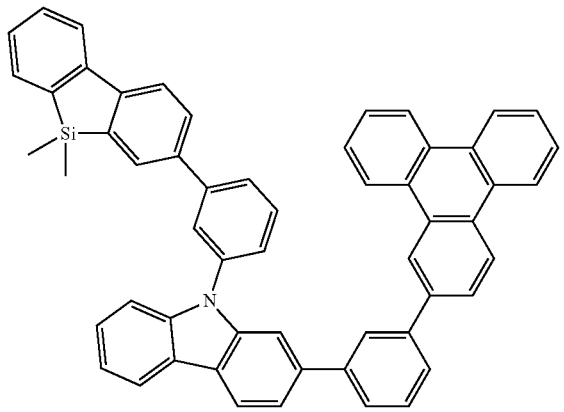
Chemical Formula 1-8
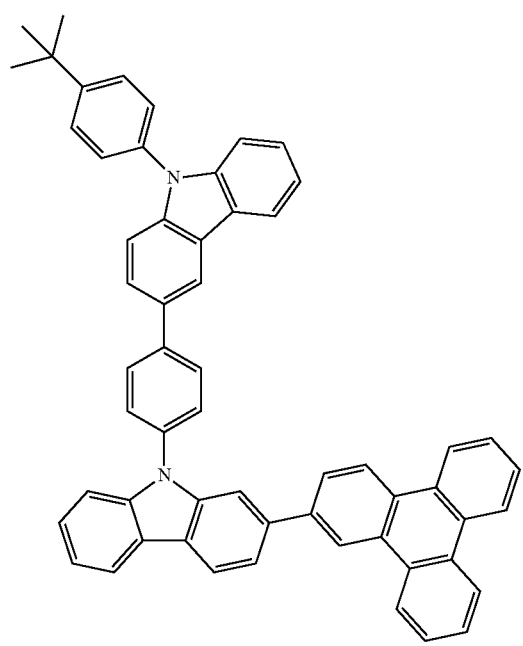
Chemical Formula 1-9
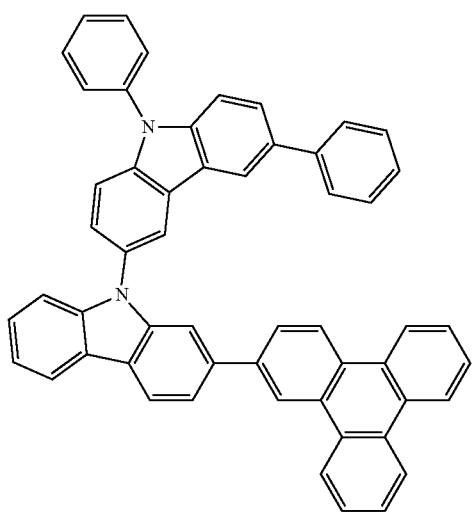

-continued
Chemical Formula 1-10
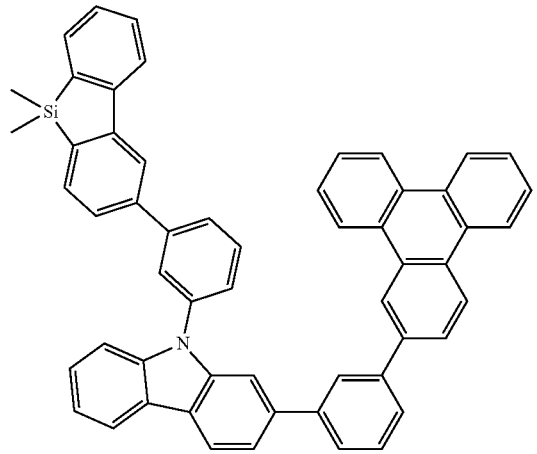
Chemical Formula 1-12
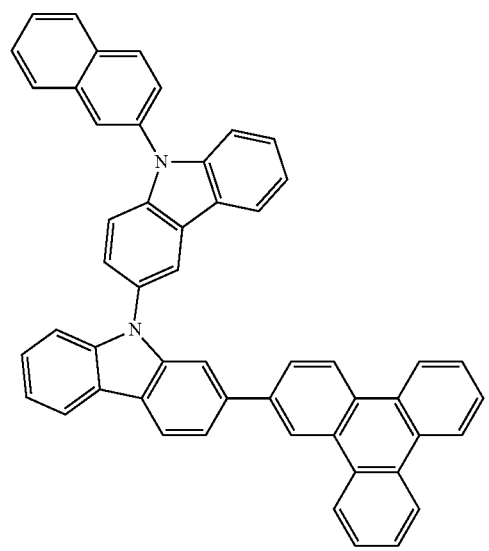
Chemical Formula 1-13
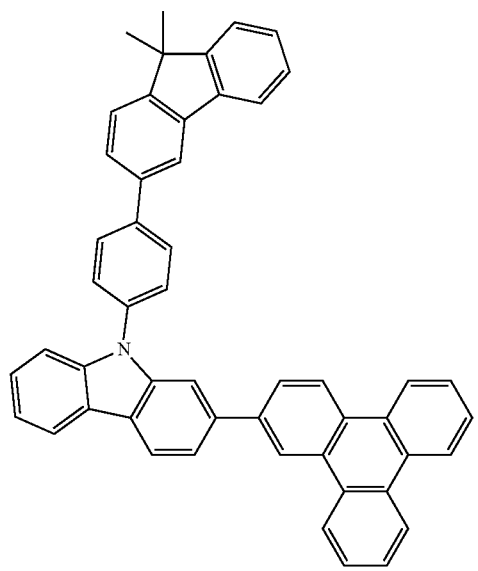
Chemical Formula 1-14
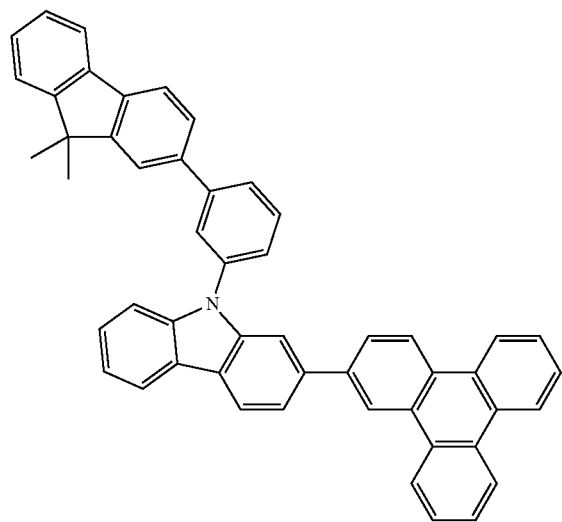
Chemical Formula 1-15
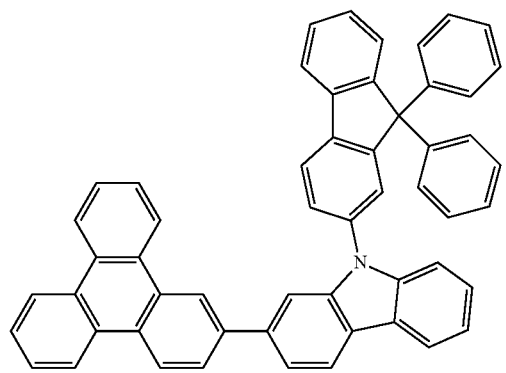

-continued
Chemical Formula 1-16
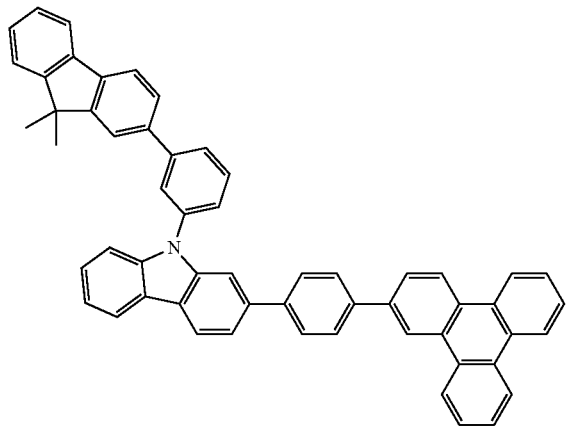
Chemical Formula 1-17
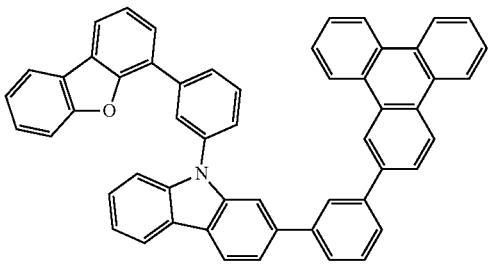
Chemical Formula 1-18
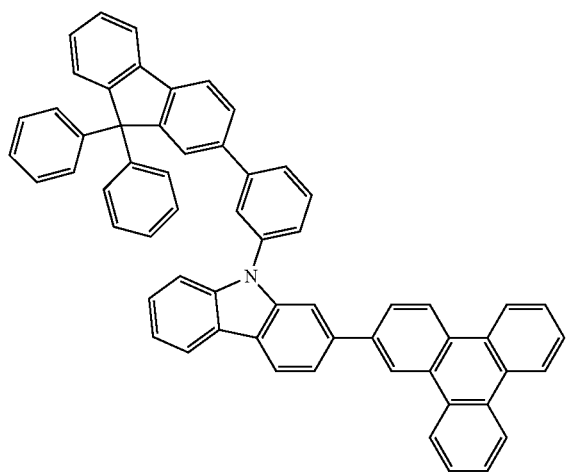
Chemical Formula 1-19
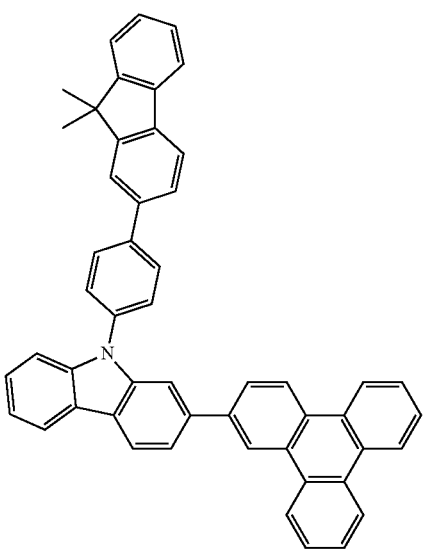
Chemical Formula 1-20
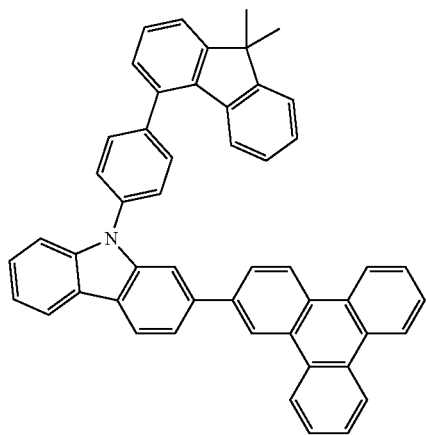
Chemical Formula 1-21
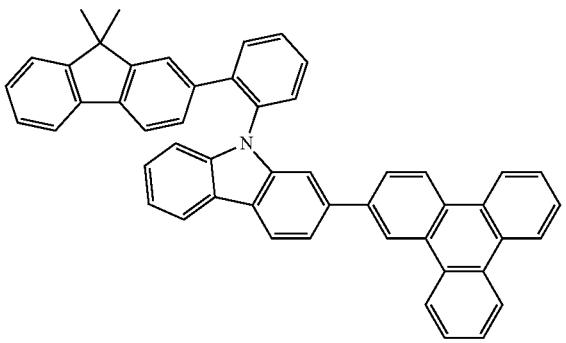

-continued
Chemical Formula 1-22
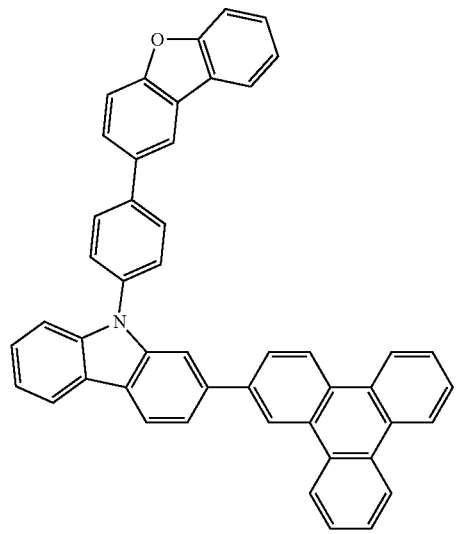
Chemical Formula 1-23
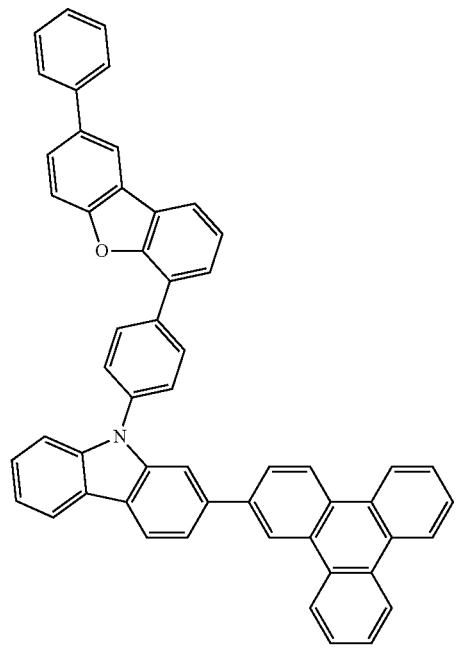
Chemical Formula 1-24
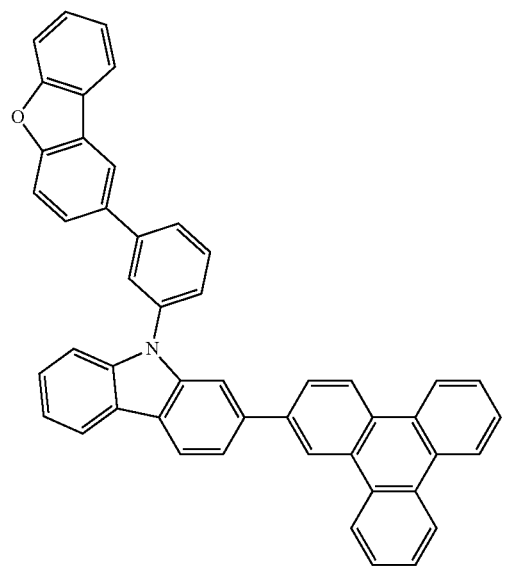
Chemical Formula 1-25
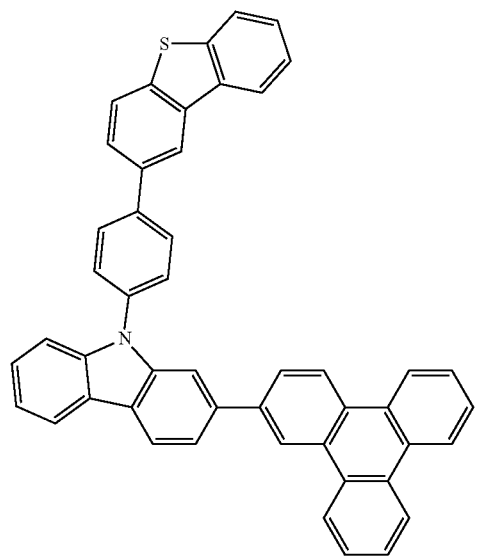

Chemical Formula 1-26
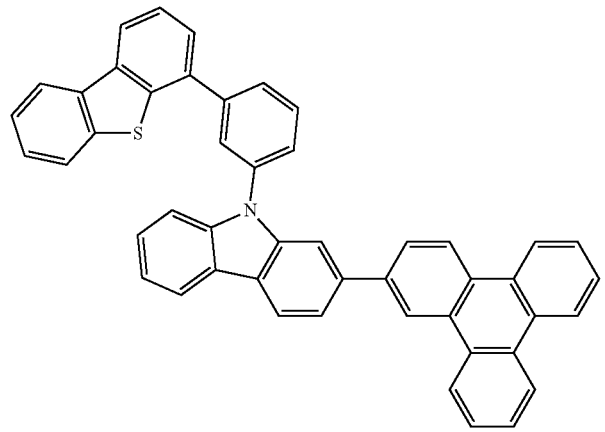
Chemical Formula 1-27
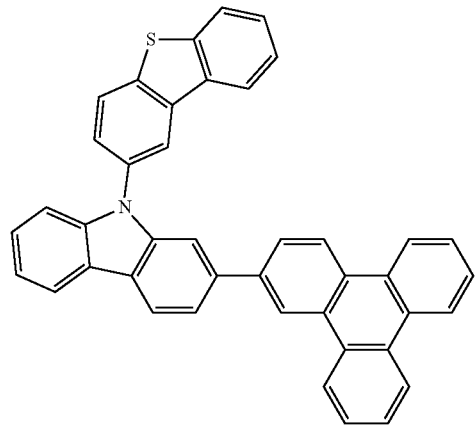
Chemical Formula 1-28
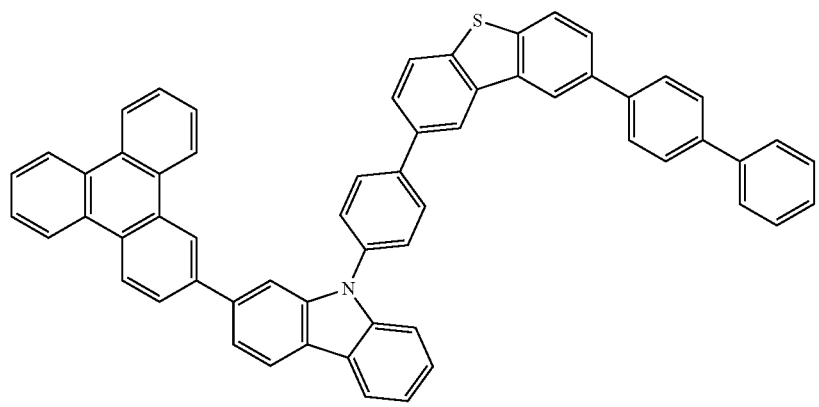
Chemical Formula 1-29
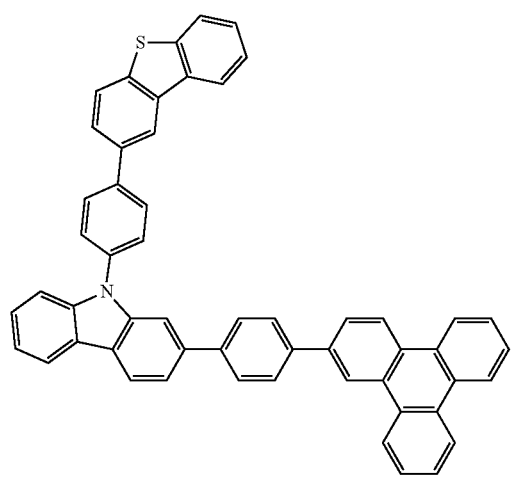
Chemical Formula 1-30
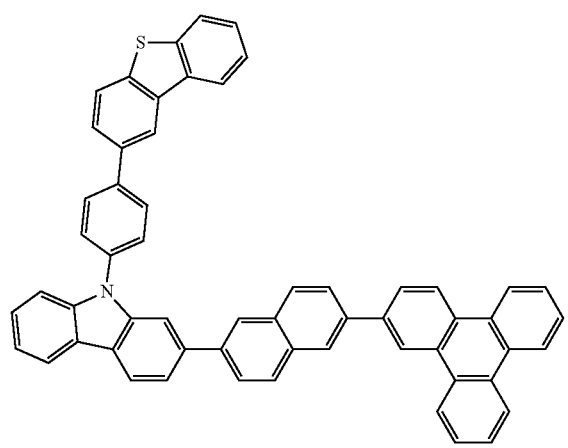

-continued
Chemical Formula 1-31
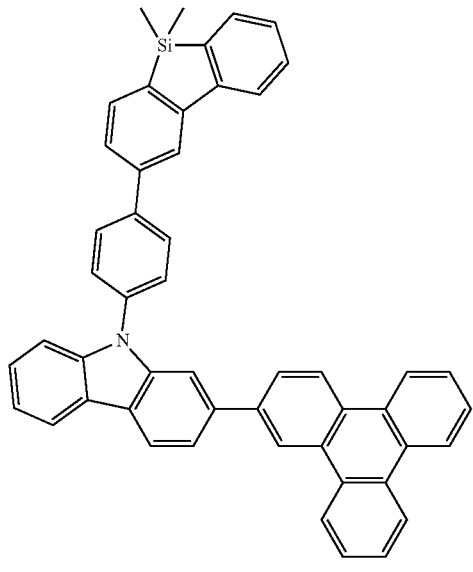
Chemical Formula 1-32
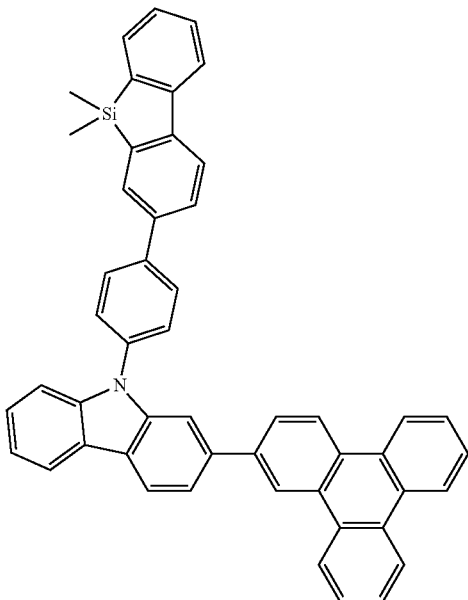
Chemical Formula 1-33
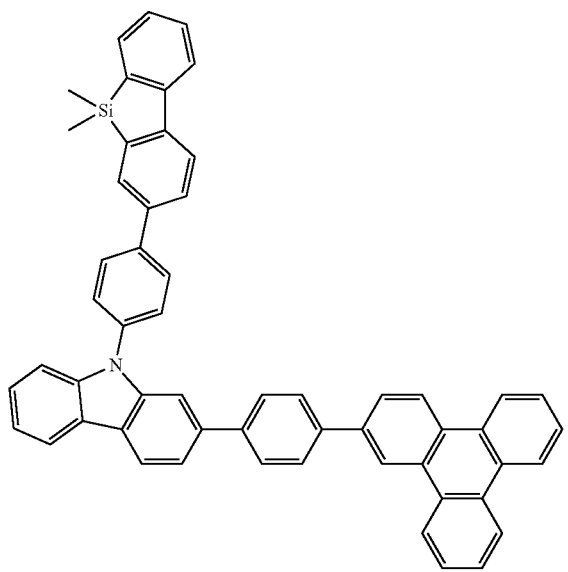
Chemical Formula 1-34

Chemical Formula 1-35
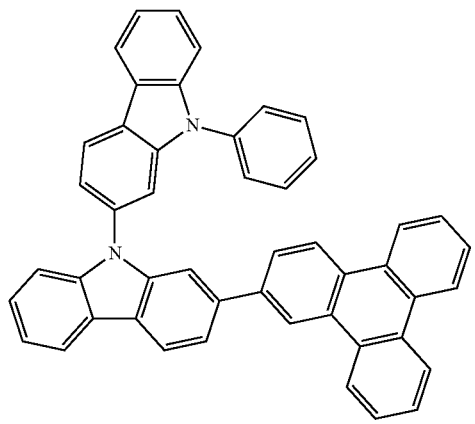
Chemical Formula 1-36
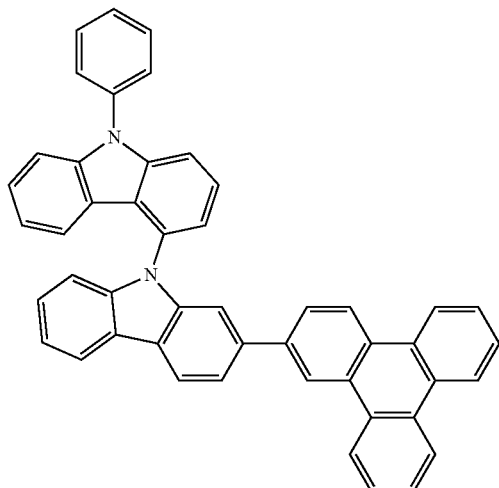
Chemical Formula 1-37
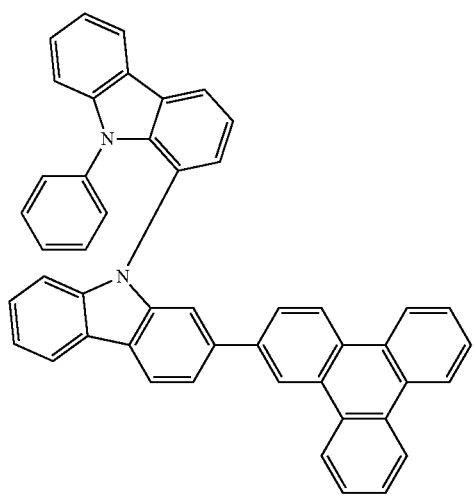
Chemical Formula 1-38
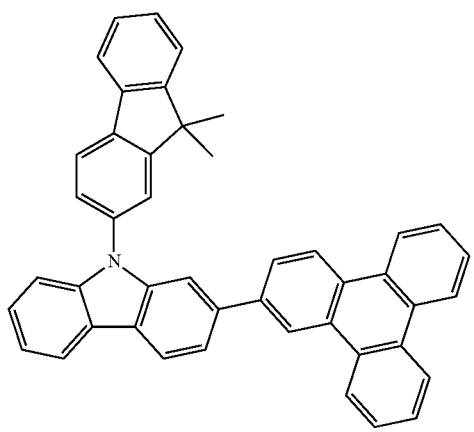
Chemical Formula 1-39
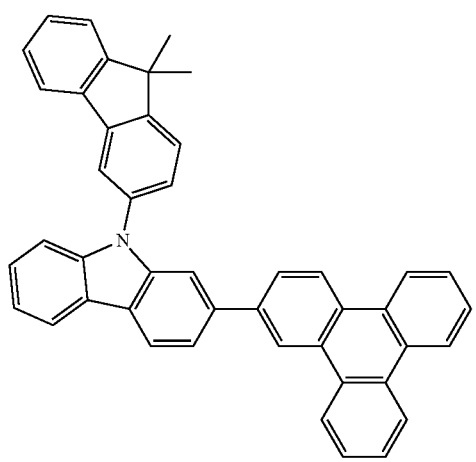
Chemical Formula 1-40
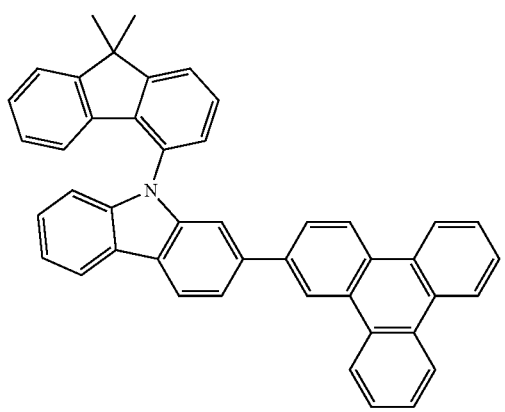

Chemical Formula 1-41
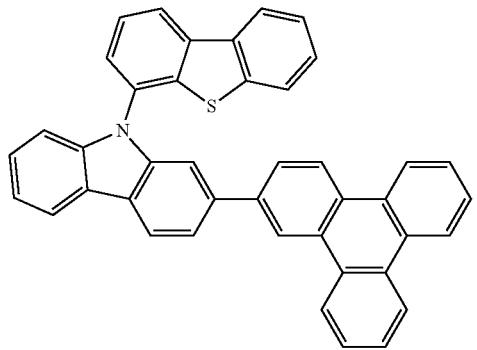
Chemical Formula 1-42
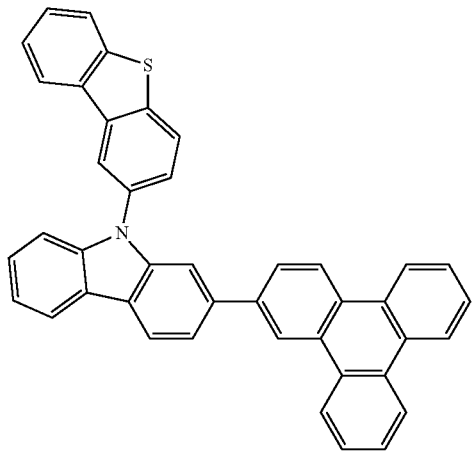
Chemical Formula 1-43
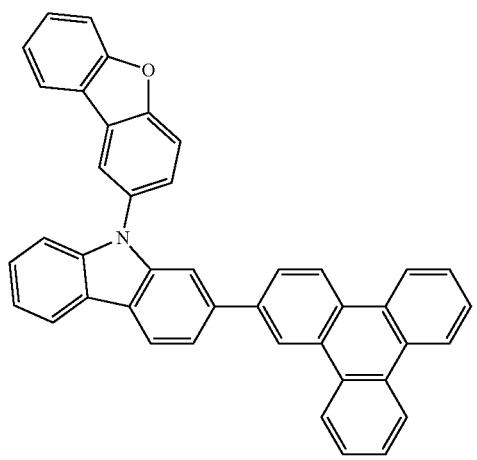
Chemical Formula 1-44
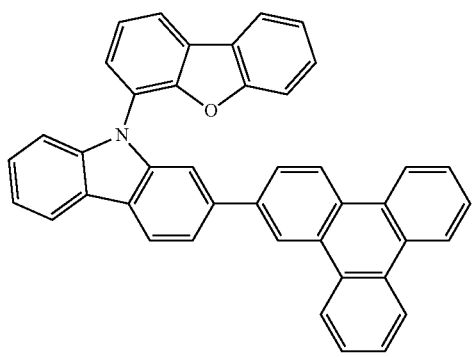
Chemical Formula 1-45
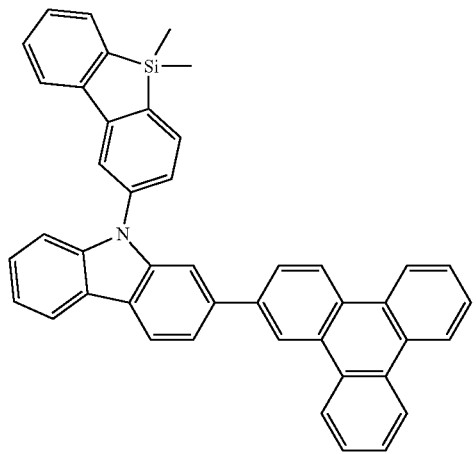
Chemical Formula 1-46
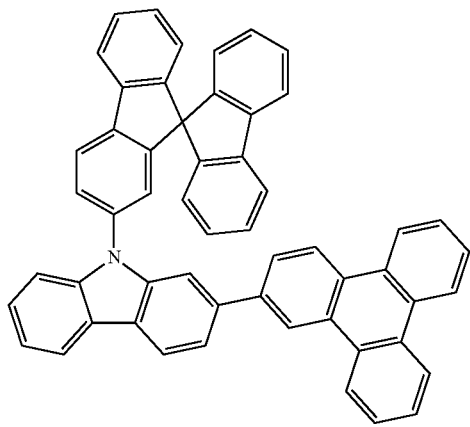

-continued
Chemical Formula 1-47
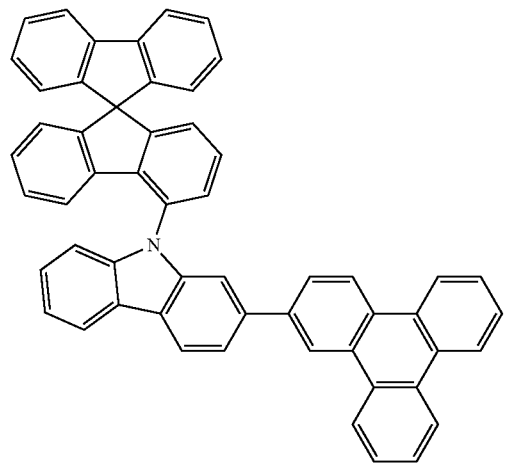
Chemical Formula 1-48
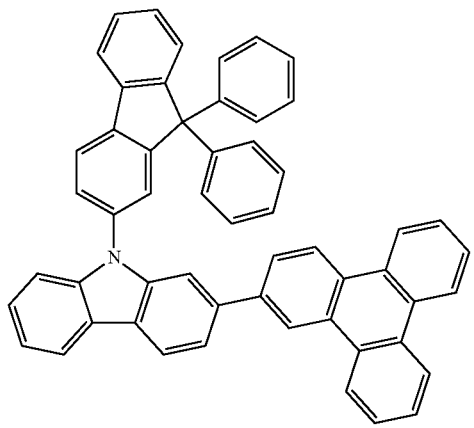
Chemical Formula 1-49
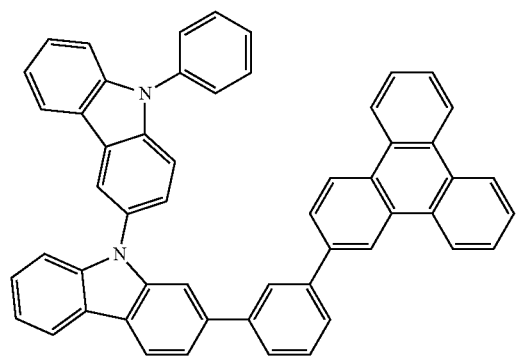
Chemical Formula 1-50
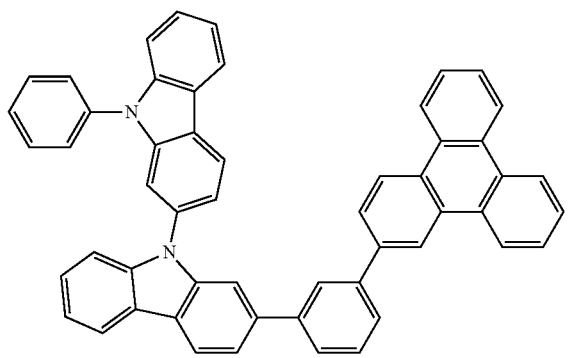
Chemical Formula 1-51
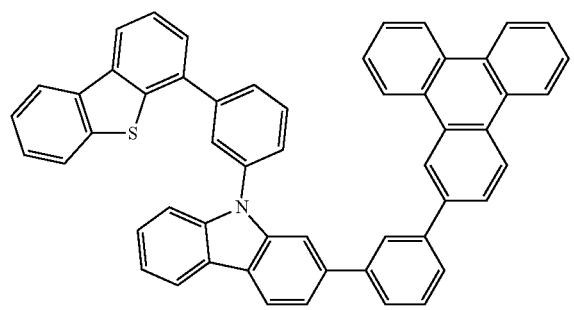
Chemical Formula 1-52
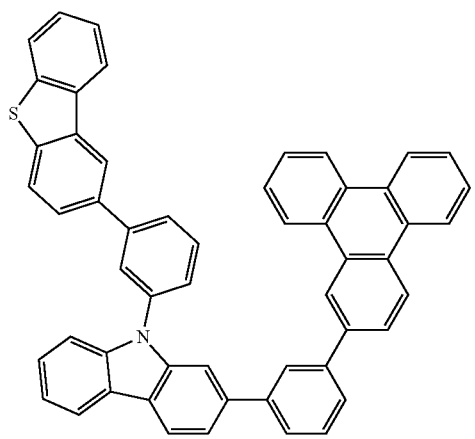

-continued
Chemical Formula 1-53
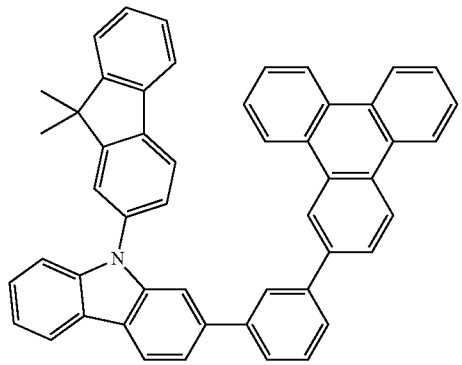
Chemical Formula 1-54
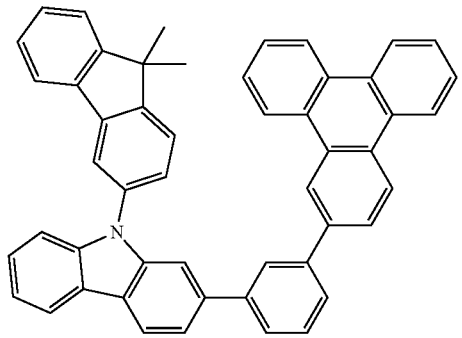
Chemical Formula 1-55
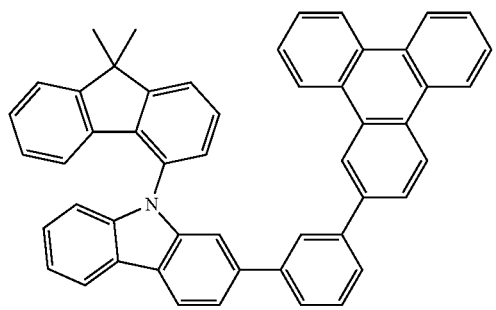
Chemical Formula 1-56
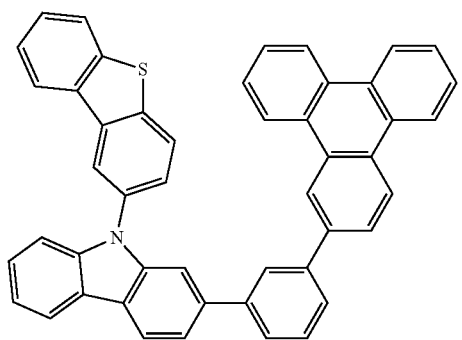
Chemical Formula 1-57
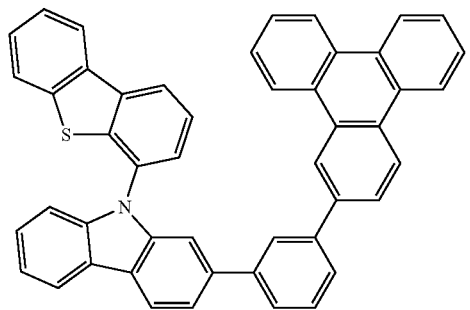
Chemical Formula 1-58
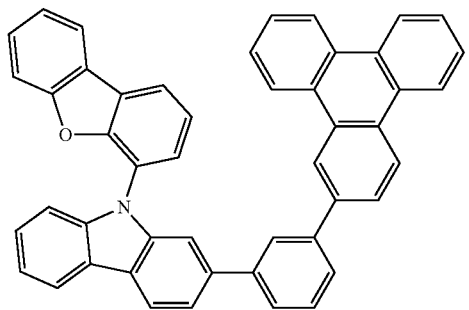
Chemical Formula 1-59
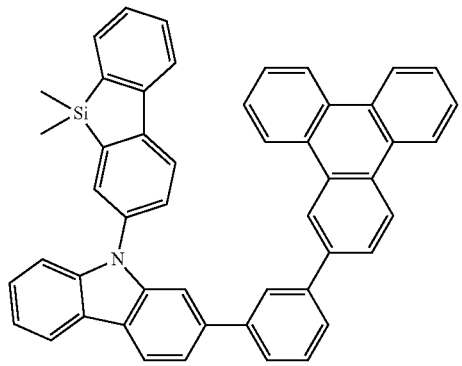
Chemical Formula 1-60
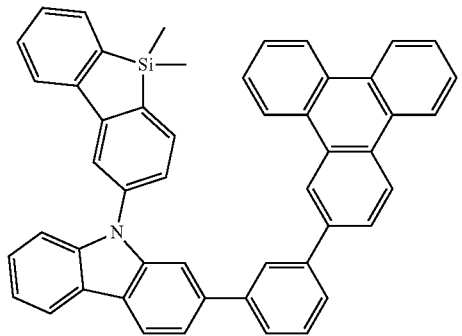

-continued
Chemical Formula 1-61
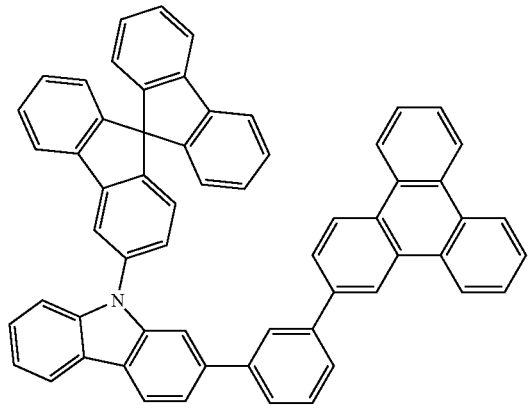
Chemical Formula 1-62
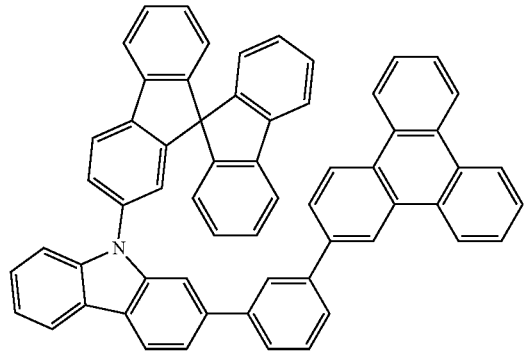
Chemical Formula 1-63
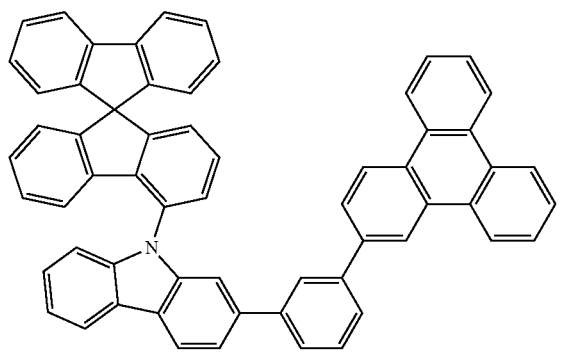
Chemical Formula 1-68
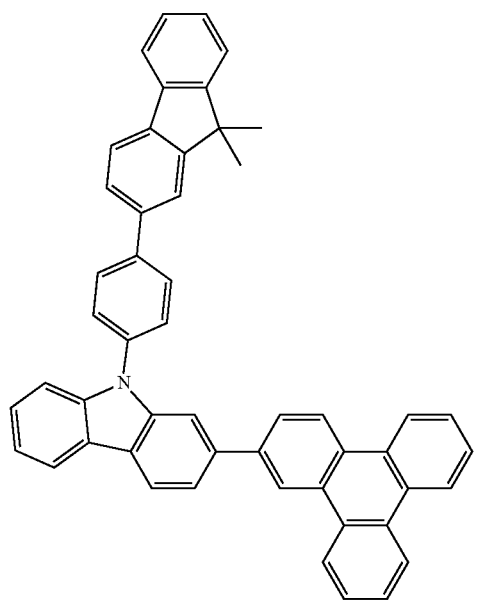

-continued
Chemical Formula 1-69
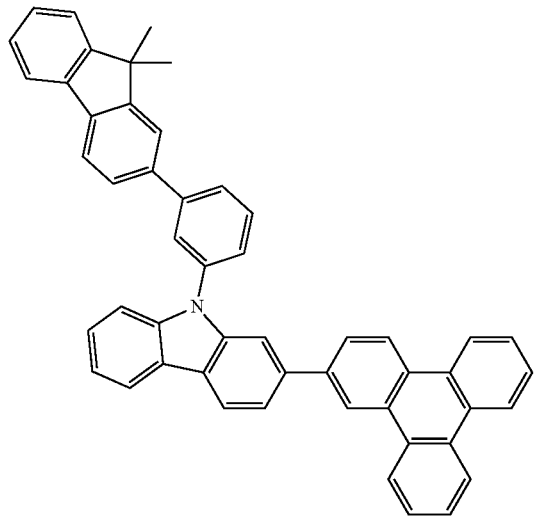
Chemical Formula 1-70
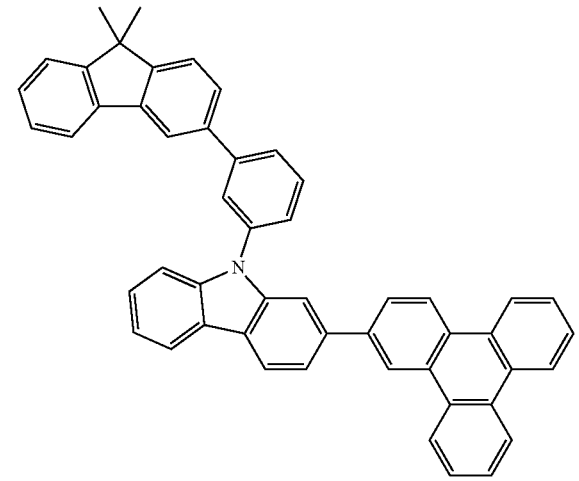
Chemical Formula 1-71
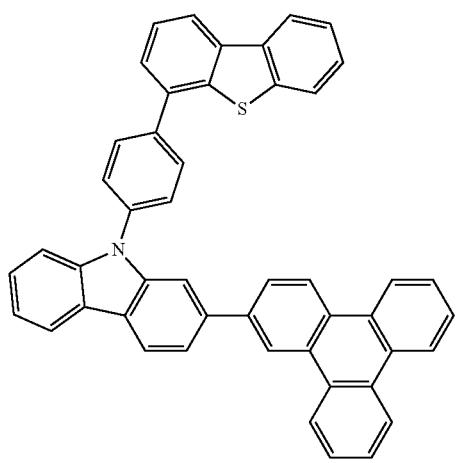
Chemical Formula 1-72
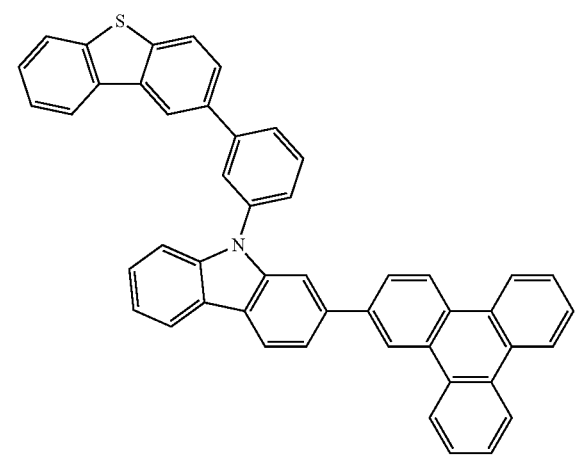
Chemical Formula 1-73
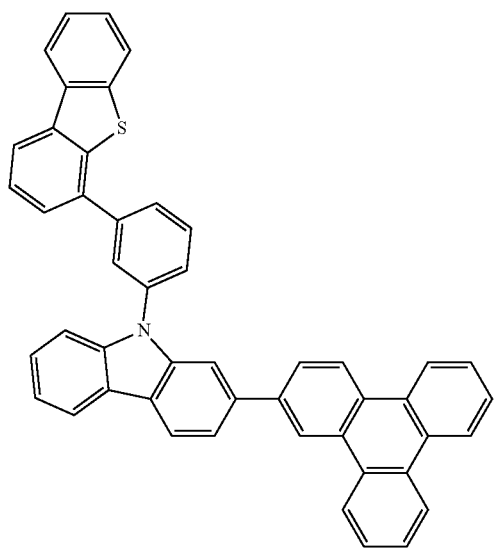
Chemical Formula 1-74
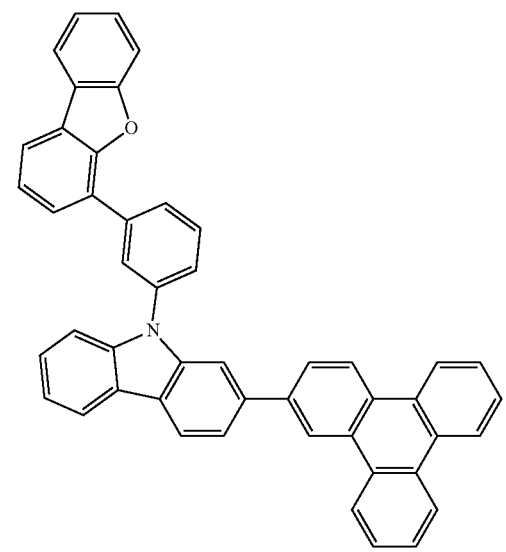

-continued
Chemical Formula 1-75
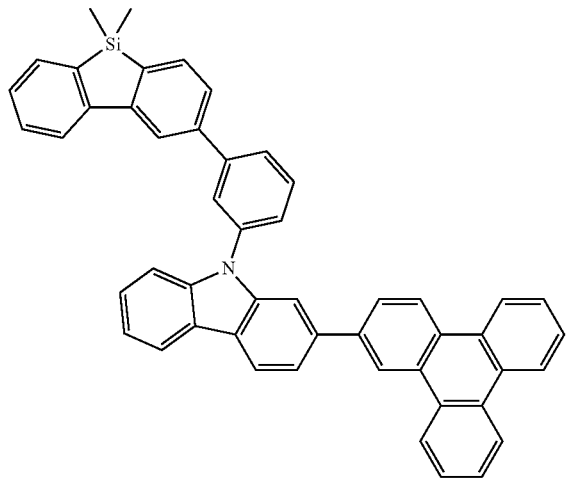
Chemical Formula 1-76
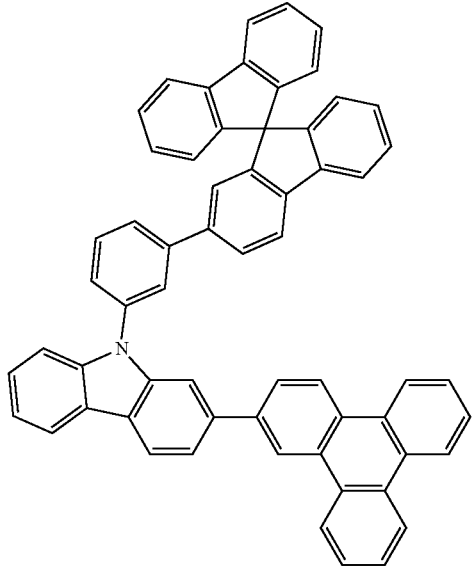
Chemical Formula 1-77
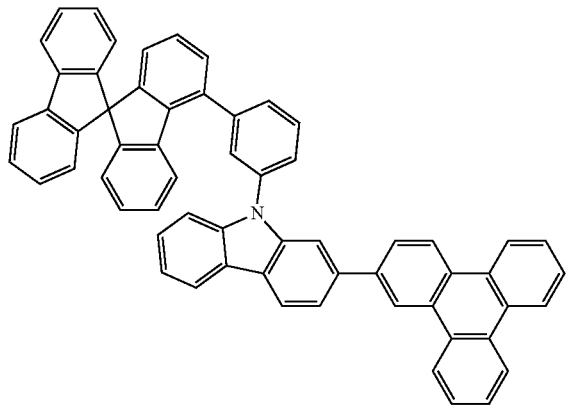
Chemical Formula 1-78
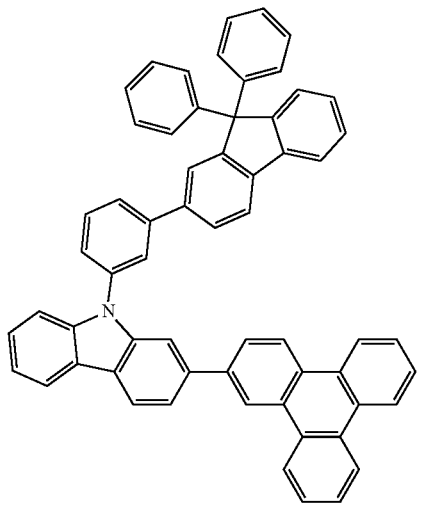
Chemical Formula 1-79
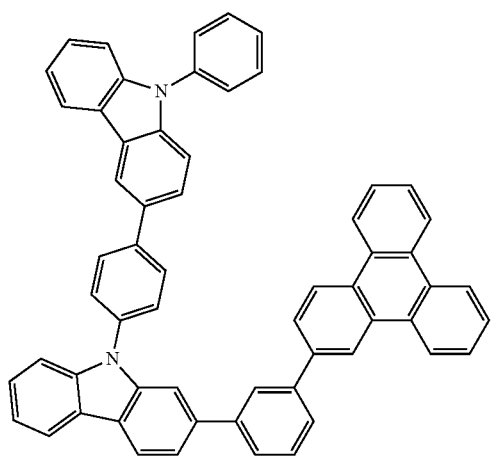
Chemical Formula 1-80
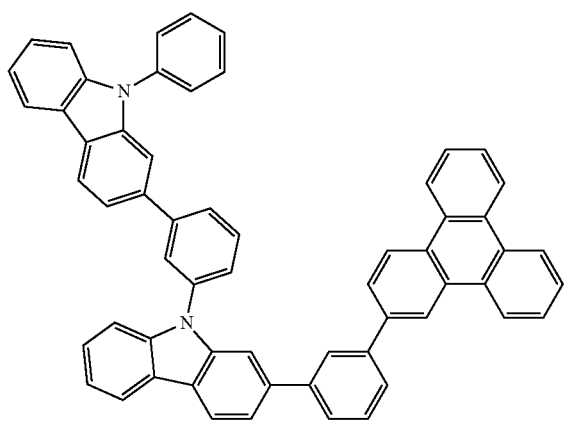

-continued

Chemical Formula 1-81

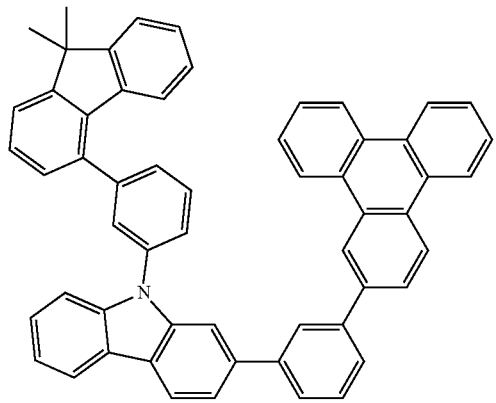

Chemical Formula 1-82

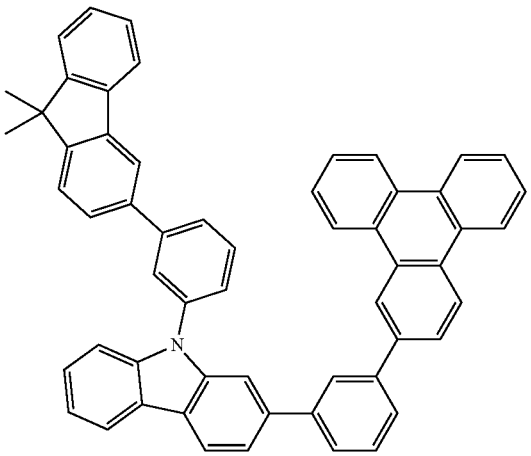

Chemical Formula 1-83

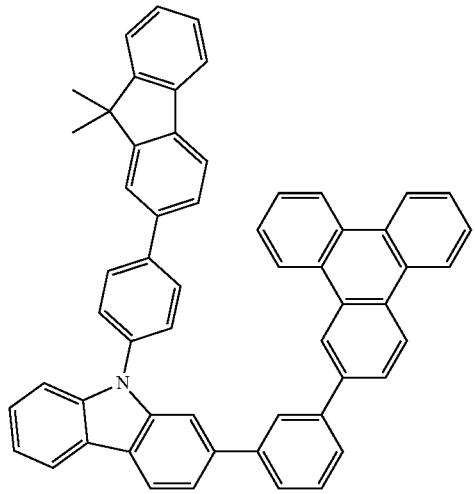

Chemical Formula 1-84

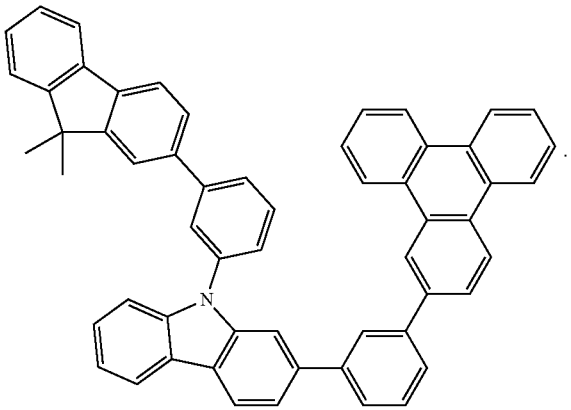

8. An organic light emitting device comprising:
a first electrode;
a second electrode provided opposite to the first electrode; and
one or more organic material layers provided between the first electrode and the second electrode,
wherein one or more layers of the organic material layers include the compound of claim 1.

9. The organic light emitting device of claim 8, wherein the organic material layer including the compound is a hole injection layer; a hole transfer layer; or a hole injection and transfer layer.

10. The organic light emitting device of claim 8, wherein the organic material layer including the compound is an electron injection layer; an electron transfer layer; or an electron injection and transfer layer.

11. The organic light emitting device of claim 8, wherein the organic material layer including the compound is a light emitting layer.

12. An organic light emitting device comprising:
a first electrode;
a second electrode provided opposite to the first electrode; and
one or more organic material layers provided between the first electrode and the second electrode,
wherein one or more layers of the organic material layers include the compound of claim 7.

* * * * *